(12) United States Patent
Adamer et al.

(10) Patent No.: US 11,040,986 B2
(45) Date of Patent: Jun. 22, 2021

(54) CRYSTALLINE FORMS OF CABOTEGRAVIR SODIUM

(71) Applicant: Sandoz AG, Basel (CH)

(72) Inventors: Verena Adamer, Kundl (AT); Andrea Thaler, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/485,541

(22) PCT Filed: Jan. 25, 2018

(86) PCT No.: PCT/EP2018/051819
§ 371 (c)(1),
(2) Date: Aug. 13, 2019

(87) PCT Pub. No.: WO2018/149608
PCT Pub. Date: Aug. 23, 2018

(65) Prior Publication Data
US 2020/0385401 A1    Dec. 10, 2020

(30) Foreign Application Priority Data

Feb. 16, 2017 (EP) .................................. 17156518
Mar. 16, 2017 (EP) .................................. 17161414

(51) Int. Cl.
*C07D 498/14* (2006.01)

(52) U.S. Cl.
CPC ........ *C07D 498/14* (2013.01); *C07B 2200/13* (2013.01)

(58) Field of Classification Search
CPC .......................... C07D 498/14; C07B 2200/13
USPC .......................................... 544/346; 514/249
See application file for complete search history.

(56) References Cited

FOREIGN PATENT DOCUMENTS

| EP | 3045206 A1 | 7/2016 | | |
|---|---|---|---|---|
| WO | 2005100364 A1 | 10/2005 | | |
| WO | 2006116764 A1 | 11/2006 | | |
| WO | 2010068253 A1 | 6/2010 | | |
| WO | 2011119566 A1 | 9/2011 | | |
| WO | 2015139591 A1 | 9/2015 | | |
| WO | 2015177537 A1 | 11/2015 | | |
| WO | WO2018/109786 | * | 6/2018 | ........... C07D 498/14 |

OTHER PUBLICATIONS

International Search Report and Written Opinion for PCT/EP2018/051819, dated Aug. 23, 2018, 12 pages.
Johns, Brian A., et al., J. Med. Chem., 56, 2013, pp. 5901-5916.
Pecharsky, et al., Fundamentals of Powder Diffraction and Structural Characterization of Materials, Springer, 2005, p. 3.
Lee, Eun Hee, A practical guide to pharmaceutical polymorph screening & selection, Asian Journal of Pharmaceutical Sciences, 2014, vol. 9, No. 4, pp. 163-175.
Llinas, Antonio, et al., Polymorph control: past, present and future, Drug Discovery Today, 2008, vol. 13, No. 5/6, pp. 198-210.
Reutzel-Edens, Susan M., Achieving polymorph selectivity in the crystallization of pharmaceutical solids: Basic considerations and recent advances, Current opinion in drug discovery and development, 2006, vol. 9, No. 6, pp. 806-815.
Xu, Dong, et al., Statistical cluster analysis of pharmaceutical solvents, International Journal of Pharmaceutics, 2007, vol. 339, pp. 175-188.
Brittain, H.G, Polymorphism in Pharmaceutical Solids, Marcel Dekker, Inc., New York, 2009, Edited by Brittain, pp. 333-334 (provided as full chapter by Australian Patent Office).
U.S. Pharmacopeia, Harmonization Stage 6, https://www.usp.org/sites/default/files/usp/document/harmonization/gen-chapter/g14_pf_35_3_2009.pdf, accessed Apr. 12, 2021.

* cited by examiner

*Primary Examiner* — Jeffrey H Murray
(74) *Attorney, Agent, or Firm* — Luedeka Neely Group, P.C,

(57) ABSTRACT

The present invention relates to crystalline forms of cabotegravir sodium and to methods for their preparation. Furthermore, the invention relates to a pharmaceutical composition comprising one of said crystalline forms of cabotegravir sodium, preferably in a predetermined and/or effective amount, and at least one pharmaceutically acceptable excipient. The pharmaceutical composition of the present invention can be used as a medicament, in particular for the treatment and/or prophylaxis of viral infections such as HIV infections.

11 Claims, 10 Drawing Sheets

CRYSTALLINE FORMS OF CABOTEGRAVIR SODIUM

This application is a Section 371 national phase entry of PCT application PCT/EP2018/051819, filed Jan. 25, 2018. This application also claims the benefit of the earlier filing dates of European patent application 17156518.7, filed Feb. 16, 2017, and of European patent application 17161414.2, filed Mar. 16, 2017.

FIELD OF THE INVENTION

The present invention relates to crystalline forms of cabotegravir sodium and to processes for their preparation. Furthermore, the invention relates to a pharmaceutical composition comprising one of said crystalline forms of cabotegravir sodium, preferably in a predetermined and/or effective amount, and at least one pharmaceutically acceptable excipient. The pharmaceutical composition of the present invention can be used as a medicament, in particular for the treatment and/or prophylaxis of viral infections such as HIV infections.

BACKGROUND OF THE INVENTION

Cabotegravir is a human immunodeficiency virus type 1 (HIV-1) integrase strand transfer inhibitor (INSTI) currently under development for the treatment of HIV-1 infection in combination with other antiretroviral agents. It is chemically designated as (3S,11aR)-N-[2,4-Difluorophenyl)methyl]-6-hydroxy-3-methyl-5,7-dioxo-2,3,5,7,11,11a-hexahydro[1,3]oxazolo [3,2-a]pyrido [1,2-d]pyrazine-8-carboxamide and can be represented by the following chemical structure according to Formula (I)

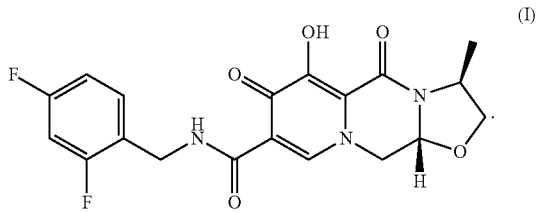 [SMILES: C[C@H]1CO[C@@H]2Cn3cc(C(=O)NCc4ccc(F)cc4F)c(=O)c(O)c3C(=O)N12]

A process for the preparation of cabotegravir sodium is disclosed in Example Z-9 of WO 2006/116764 A1, where cabotegravir was treated with 1 N sodium hydroxide in ethanol followed by ether addition. In Example Ae of WO 2010/068253 A1 cabotegravir is dissolved in aqueous ethanol and reacted with 1 N aqueous sodium hydroxide solution at 75° C. to the corresponding sodium salt. Cooling the solution followed by filtration, washing with ethanol and drying provided cabotegravir sodium as crystals. In Johns B. A. et. al Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744). J. Med. Chem. 2013, 56, 5901-5916 cabotegravir was treated with 1 N aqueous sodium hydroxide in ethanol to obtain cabotegravir sodium as a white solid. In Example 17 of WO 2015/177537 A1 cabotegravir sodium was prepared by treating cabotegravir with 2 N aqueous sodium hydroxide in methanol.

The inventors of the present invention repeated the above listed prior art examples (see Reference Examples 1 to 4 herein). According to powder X-ray diffraction the same crystalline form of cabotegravir sodium was obtained in all cases. This form is designated as "Form A" herein.

Different solid state forms of an active pharmaceutical ingredient often possess different properties. Differences in the physicochemical properties of solid state forms can be important for the improvement of pharmaceutical compositions, for example, pharmaceutical formulations with improved dissolution profile or with improved stability or shelf-life can become accessible due to an improved solid state form of an active pharmaceutical ingredient. Also processing or handling of the active pharmaceutical ingredient during the formulation process may be improved. New solid state forms of an active pharmaceutical ingredient can thus have desirable processing properties. They can be easier to handle, better suited for storage, and/or allow for better purification, compared to previously known solid state forms.

Furthermore, the sudden appearance or disappearance of a metastable polymorph can present a problem in pharmaceutical development. Similarly, serious pharmaceutical consequences arise if transformation occurs in a dosage form, e.g. upon storage. It is therefore desirable to use a stable polymorph, e.g. a kinetically stable polymorph or preferably the thermodynamically most stable polymorph of an active pharmaceutical ingredient for the preparation of a drug product. Hence, there is a strong need for the provision of a solid form of cabotegravir sodium which is stable, such as thermodynamically stable, and does not undergo phase transformation during production, pharmaceutical processing or storage. There is also a strong need for the provision of a pharmaceutical composition comprising a solid form of cabotegravir sodium, which is stable at the conditions typically encountered during pharmaceutical processing and storage. A polymorph, which is kinetically more stable than the prior art polymorph, and the thermodynamically most stable solid form in particular can ensure reliable efficacy and safety for the whole duration of a pharmaceutical composition's shelf-life.

SUMMARY OF THE INVENTION

The inventors of the present invention surprisingly identified polymorphs of cabotegravir sodium, which are thermodynamically more stable at room temperature and elevated temperatures than the prior art "Form A". These forms are hereinafter referred to as "Form B" and "Form C". Aspects, advantageous features and preferred embodiments of the present invention are summarized in the following items:

1) A crystalline form of cabotegravir sodium characterized by having a powder X-ray diffractogram comprising reflections at 2-Theta angles of (6.8±0.2)°, (18.5±0.2)° and (23.7±0.2)°, when measured at a temperature in the range of from 20 to 30° C. with Cu-Kalpha$_{1,2}$ radiation having a wavelength of 0.15419 nm.

2) A crystalline form of cabotegravir sodium characterized by having a powder X-ray diffractogram comprising reflections at 2-Theta angles of (6.8±0.2)°, (18.5±0.2)°, (20.3±0.2)° and (23.7±0.2)°, when measured at a temperature in the range of from 20 to 30° C. with Cu-Kalpha$_{1,2}$ radiation having a wavelength of 0.15419 nm.

3) A crystalline form of cabotegravir sodium characterized by having a powder X-ray diffractogram comprising reflections at 2-Theta angles of (6.8±0.2)°, (18.5±0.2)°, (18.9±0.2)°, (20.3±0.2)° and (23.7±0.2)°, when measured at a temperature in the range of from 20 to 30° C. with Cu-Kalpha$_{1,2}$ radiation having a wavelength of 0.15419 nm.

4) A crystalline form of cabotegravir sodium characterized by having a powder X-ray diffractogram comprising reflections at 2-Theta angles of (6.8±0.2)°, (18.5±0.2)°, (18.9±0.2)°, (20.3±0.2)°, (22.8±0.2)° and (23.7±0.2)°, when measured at a temperature in the range of from 20 to 30° C. with Cu-Kalpha$_{1,2}$ radiation having a wavelength of 0.15419 nm.

5) A crystalline form of cabotegravir sodium characterized by having a powder X-ray diffractogram comprising reflections at 2-Theta angles (6.8±0.2)°, (18.5±0.2)°, (18.9±0.2)°, (20.3±0.2)°, (22.8±0.2)°, (23.2±0.2)° and (23.7±0.2)°, when measured at a temperature in the range of from 20 to 30° C. with Cu-Kalpha$_{1,2}$ radiation having a wavelength of 0.15419 nm.

6) A crystalline form of cabotegravir sodium characterized by having a powder X-ray diffractogram comprising reflections at 2-Theta angles of (6.8±0.2)°, (17.7±0.2)°, (18.5±0.2)°, (18.9±0.2)°, (20.3±0.2)°, (22.8±0.2)°, (23.2±0.2)° and (23.7±0.2)°, when measured at a temperature in the range of from 20 to 30° C. with Cu-Kalpha$_{1,2}$ radiation having a wavelength of 0.15419 nm.

7) A crystalline form of cabotegravir sodium characterized by having a powder X-ray diffractogram comprising reflections at 2-Theta angles of (6.8±0.2)°, (17.7±0.2)°, (18.5±0.2)°, (18.9±0.2)°, (20.3±0.2)°, (20.6±0.2)°, (22.8±0.2)°, (23.2±0.2)° and (23.7±0.2)°, when measured at a temperature in the range of from 20 to 30° C. with Cu-Kalpha$_{1,2}$ radiation having a wavelength of 0.15419 nm.

8) A crystalline form of cabotegravir sodium characterized by having a powder X-ray diffractogram comprising reflections at 2-Theta angles of (6.8±0.2)°, (17.7±0.2)°, (18.5±0.2)°, (18.9±0.2)°, (20.3±0.2)°, (20.6±0.2)°, (22.8±0.2)°, (23.2±0.2)°, (23.7±0.2)° and (28.6±0.2)°, when measured at a temperature in the range of from 20 to 30° C. with Cu-Kalpha$_{1,2}$ radiation having a wavelength of 0.15419 nm.

9) A crystalline form of cabotegravir sodium characterized by having a powder X-ray diffractogram comprising reflections at 2-Theta angles of (6.8±0.2)°, (14.6±0.2)°, (17.7±0.2)°, (18.5±0.2)°, (18.9±0.2)°, (20.3±0.2)°, (20.±0.2)°, (22.8±0.2)°, (23.2±0.2)°, (23.7±0.2)° and (28.6±0.2)°, when measured at a temperature in the range of from 20 to 30° C. with Cu-Kalpha$_{1,2}$ radiation having a wavelength of 0.15419 nm.

10) A crystalline form of cabotegravir sodium characterized by having a powder X-ray diffractogram comprising reflections at 2-Theta angles of (6.8±0.2)°, (14.6±0.2)°, (17.7±0.2)°, (18.5±0.2)°, (18.9±0.2)°, (20.3±0.2)°, (20.6±0.2)°, (22.8±0.2)°, (23.2±0.2)°, (23.7±0.2)°, (27.3±0.2)° and (28.6±0.2)°, when measured at a temperature in the range of from 20 to 30° C. with Cu-Kalpha$_{1,2}$ radiation having a wavelength of 0.15419 nm.

11) A crystalline form of cabotegravir sodium characterized by having a powder X-ray diffractogram comprising reflections at 2-Theta angles of (6.8±0.1)°, (18.5±0.1)° and (23.7±0.1)°, when measured at a temperature in the range of from 20 to 30° C. with Cu-Kalpha$_{1,2}$ radiation having a wavelength of 0.15419 nm.

12) A crystalline form of cabotegravir sodium characterized by having a powder X-ray diffractogram comprising reflections at 2-Theta angles of (6.8±0.1)°, (18.5±0.1)°, (20.3±0.1)° and (23.7±0.1)°, when measured at a temperature in the range of from 20 to 30° C. with Cu-Kalpha$_{1,2}$ radiation having a wavelength of 0.15419 nm.

13) A crystalline form of cabotegravir sodium characterized by having a powder X-ray diffractogram comprising reflections at 2-Theta angles of (6.8±0.1)°, (18.5±0.1)°, (18.9±0.1)°, (20.3±0.1)° and (23.7±0.1)°, when measured at a temperature in the range of from 20 to 30° C. with Cu-Kalpha$_{1,2}$ radiation having a wavelength of 0.15419 nm.

14) A crystalline form of cabotegravir sodium characterized by having a powder X-ray diffractogram comprising reflections at 2-Theta angles of (6.8±0.1)°, (18.5±0.1)°, (18.9±0.1)°, (20.3±0.1)°, (22.8±0.1)° and (23.7±0.1)°, when measured at a temperature in the range of from 20 to 30° C. with Cu-Kalpha$_{1,2}$ radiation having a wavelength of 0.15419 nm.

15) A crystalline form of cabotegravir sodium characterized by having a powder X-ray diffractogram comprising reflections at 2-Theta angles (6.8±0.1)°, (18.5±0.1)°, (18.9±0.1)°, (20.3±0.1)°, (22.8±0.1)°, (23.2±0.1)° and (23.7±0.1)°, when measured at a temperature in the range of from 20 to 30° C. with Cu-Kalpha$_{1,2}$ radiation having a wavelength of 0.15419 nm.

16) A crystalline form of cabotegravir sodium characterized by having a powder X-ray diffractogram comprising reflections at 2-Theta angles of (6.8±0.1)°, (17.7±0.1)°, (18.5±0.1)°, (18.9±0.1)°, (20.3±0.1)°, (22.8±0.1)°, (23.2±0.1)° and (23.7±0.1)°, when measured at a temperature in the range of from 20 to 30° C. with Cu-Kalpha$_{1,2}$ radiation having a wavelength of 0.15419 nm.

17) A crystalline form of cabotegravir sodium characterized by having a powder X-ray diffractogram comprising reflections at 2-Theta angles of (6.8±0.1)°, (17.7±0.1)°, (18.5±0.1)°, (18.9±0.1)°, (20.3±0.1)°, (20.6±0.1)°, (22.8±0.1)°, (23.2±0.1)° and (23.7±0.1)°, when measured at a temperature in the range of from 20 to 30° C. with Cu-Kalpha$_{1,2}$ radiation having a wavelength of 0.15419 nm.

18) A crystalline form of cabotegravir sodium characterized by having a powder X-ray diffractogram comprising reflections at 2-Theta angles of (6.8±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)° and (28.6±0.1)°, when measured at a temperature in the range of from 20 to 30° C. with Cu-Kalpha$_{1,2}$ radiation having a wavelength of 0.15419 nm.

19) A crystalline form of cabotegravir sodium characterized by having a powder X-ray diffractogram comprising reflections at 2-Theta angles of (6.8±0.1)°, (14.6±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)° and (28.6±0.1)°, when measured at a temperature in the range of from 20 to 30° C. with Cu-Kalpha$_{1,2}$ radiation having a wavelength of 0.15419 nm.

20) A crystalline form of cabotegravir sodium characterized by having a powder X-ray diffractogram comprising reflections at 2-Theta angles of (6.8±0.1)°, (14.6±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)°, (27.3±0.1)° and (28.6±0.1)°, when measured at a temperature in the range of from 20 to 30° C. with Cu-Kalpha$_{1,2}$ radiation having a wavelength of 0.15419 nm.
21) A crystalline form of cabotegravir sodium characterized by having a powder X-ray diffractogram essentially the same as shown in FIG. 1 of the present invention, when measured at a temperature in the range of from 20 to 30° C. with Cu-Kalpha$_{1,2}$ radiation having a wavelength of 0.15419 nm.
22) A composition comprising the crystalline form of cabotegravir sodium according to any one of the preceding items, which composition is essentially free of any other physical form of cabotegravir sodium.
23) A composition comprising the crystalline form of cabotegravir sodium according to any one of items 1 to 21, characterized by comprising at most 20 weight % of any other physical form of cabotegravir sodium, based on the weight of the composition.
24) A composition comprising the crystalline form of cabotegravir sodium according to any one of items 1 to 21, characterized by comprising at most 10 weight % of any other physical form of cabotegravir sodium, based on the weight of the composition.
25) A composition comprising the crystalline form of cabotegravir sodium according to any one of items 1 to 21, characterized by comprising at most 5 weight % of any other physical form of cabotegravir sodium, based on the weight of the composition.
26) A composition comprising the crystalline form of cabotegravir sodium according to any one of items 1 to 21, characterized by comprising at most 2 weight % of any other physical form of cabotegravir sodium, based on the weight of the composition.
27) A composition comprising the crystalline form of cabotegravir sodium according to any one of items 1 to 21, characterized by comprising at most 1 weight % of any other physical form of cabotegravir sodium, based on the weight of the composition.
28) The composition according to any one of items 22 to 27, wherein the any other physical form of cabotegravir sodium is Form A characterized by having a powder X-ray diffractogram comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.
29) The composition according to any one of items 22 to 27, wherein the any other physical form of cabotegravir sodium is amorphous.
30) A process for the preparation of the crystalline form of cabotegravir sodium as defined in any one of items 1 to 21 or the composition as defined in any one of items 22 to 29 comprising:
    (i) providing a crystalline form of cabotegravir sodium (Form A) characterized by having a PXRD comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.
    (ii) slurrying the crystalline form of cabotegravir sodium provided in step (i) in a solvent selected from the group consisting of cyclic ethers, C$_3$-C$_4$ ketones and methyl acetate or mixtures thereof, wherein the slurrying is for a time sufficient to effect transformation of cabotegravir sodium (Form A) to the crystalline form of cabotegravir sodium as defined in any one of items 1 to 21 or the composition as defined in any one of items 22 to 29.
31) The process of item 30, wherein the cyclic ethers are selected from 1,4-dioxane and tetrahydrofuran.
32) The process of item 30, wherein the C$_3$-C$_4$ ketones are selected from acetone and 2-butanone.
33) The process according to any one of items 30 to 32, wherein cabotegravir sodium concentration of the suspension provided in step (ii) is in the range of from 5 to 80 g/L.
34) The process according to any one of items 30 to 32, wherein the cabotegravir sodium concentration of the suspension provided in step (ii) is in the range of from 5 to 50 g/L.
35) The process according to any one of items 30 to 32, wherein the cabotegravir sodium concentration of the suspension provided in step (ii) is in the range of from 5 to 25 g/L.
36) The process according to any one of items 30 to 32, wherein cabotegravir sodium concentration of the suspension provided in step (ii) is 10 g/L.
37) The process according to any one of items 30 to 36, wherein slurrying is performed at a temperature in the range of from 20 to 30° C.
38) The process according to any one of items 30 to 36, wherein slurrying is performed at a temperature in the range of from 40 to 80° C.
39) The process according to any one of items 30 to 36, wherein slurrying is performed at a temperature in the range of from 40 to 60° C.
40) The process according to any one of items 30 to 39, wherein the slurrying is performed for at least 24 hours.
41) The process according to item 40, wherein the slurrying is performed for at least 120 hours.
42) The process according to any one of items 30 to 41, further comprising step (iii) separating at least a part of the crystals obtained in step (ii) from the mother liquor.
43) The process according to item 42, wherein the crystals are separated from the mother liquor by filtration, centrifugation, decantation or solvent evaporation.
44) The process according to item 42, wherein the crystals are separated from the mother liquor by filtration or centrifugation.
45) The process according to item 42, wherein the crystals are separated from the mother liquor by filtration.
46) The process according to any one of items 42 to 45, further comprising step (iv) washing the isolated crystals obtained in step (iii).
47) The process according to item 46, wherein the crystals are washed with an organic solvent and/or water.
48) The process according to item 47, wherein the organic solvent is selected from the group consisting of 1,4-dioxane, tetrahydrofuran, acetone, 2-butanone and methyl acetate or mixtures thereof.
49) The process according to any one of items 30 to 48, further comprising step (v) drying the crystals obtained in any one of steps (ii) to (iv).
50) The process according to item 49, wherein drying is performed at a temperature of 150° C. or less.
51) The process according to item 49, wherein drying is performed at a temperature of 100° C. or less.
52) The process according to item 49, wherein drying is performed at a temperature of 60° C. or less.
53) The process according to item 49, wherein drying is performed at a temperature of 40° C. or less.

54) The process according to item 49, wherein drying is performed at a temperature in the range of from 20 to 30° C.
55) The process according to any one of items 49 to 54, wherein drying is performed for a period in the range of from 1 to 72 hours.
56) The process according to any one of items 49 to 54, wherein drying is performed for a period in the range of from 2 to 48 hours.
57) The process according to any one of items 49 to 54, wherein drying is performed for a period in the range of from 4 to 24 hours.
58) The process according to any one of items 49 to 54, wherein drying is performed for a period in the range of from 6 to 18 hours.
59) Use of the crystalline form of cabotegravir sodium as defined in any one of items 1 to 21 for the preparation of a pharmaceutical composition.
60) Use of the crystalline form of cabotegravir sodium as obtained by the process according to any one of items 30 to 58 for the preparation of a pharmaceutical composition.
61) Use of the composition as defined in any one of items 22 to 29 for the preparation of a pharmaceutical composition.
62) Use of the composition as obtained by the process according to any one of items 30 to 58 for the preparation of a pharmaceutical composition.
63) The use according to any one of items 59 to 62, wherein the pharmaceutical composition is prepared by a wet or dry processing method.
64) The use according to item 63, wherein the wet processing method comprises wet granulation.
65) The use according to item 63, wherein the dry processing method comprises dry granulation or dry compaction.
66) A pharmaceutical composition comprising the crystalline form of cabotegravir sodium as defined in any one of items 1 to 21 or the composition as defined in any one of items 22 to 29 and at least one pharmaceutically acceptable excipient.
67) The pharmaceutical composition of item 66, comprising a predetermined and/or effective amount of the crystalline form of cabotegravir sodium as defined in any one of items 1 to 21 or the composition as defined in any one of items 22 to 29 and at least one pharmaceutically acceptable excipient.
68) The pharmaceutical composition of item 66 or 67 or the pharmaceutical composition of item 137, wherein the at least one pharmaceutically acceptable excipient is selected from the group consisting of carriers, fillers, diluents, lubricants, sweeteners, stabilizing agents, solubilizing agents, antioxidants and preservatives, flavouring agents, binders, colorants, osmotic agents, buffers, surfactants, disintegrants, granulating agents, coating materials and combinations thereof.
69) The pharmaceutical composition according to any one of items 66 to 68 or the pharmaceutical composition of item 137, wherein the at least one pharmaceutically acceptable excipient is selected from the group consisting of mannitol, microcrystalline cellulose, povidone, sodium starch glycolate and sodium stearyl fumarate.
70) The pharmaceutical composition according to any one of items 66 to 69, or the pharmaceutical composition of item 137, comprising one or more additional active pharmaceutical ingredient(s).
71) The pharmaceutical composition according to item 70, wherein the one or more additional pharmaceutical active ingredient(s) is/are selected from the group consisting of entry/fusion inhibitors, reverse transcriptase inhibitors (RTIs), integrase strand transfer inhibitors (INSTIs), maturation inhibitors, protease inhibitors (PIs) or any combinations thereof.
72) The pharmaceutical composition according to item 71, wherein the entry/fusion inhibitors are selected from the group consisting of enfuvirtide, maraviroc, vicriviroc, cenicriviroc, ibalizumab and fostemsavir or mixtures thereof.
73) The pharmaceutical composition according to item 71, wherein the reverse transcriptase inhibitors (RTIs) are selected from the group consisting of abacavir, didanosine, emtricitabine, lamivudine, stavudine, zidovudine, amdoxovir, apricitabine, censavudine, elvucitabine, racivir, stampidine, zalcitabine, tenofovir disoproxil, tenofovir alafenamide, efavirenz, nevirapine, delavirdine, etravirine, rilpivirine, doravirine or mixtures thereof.
74) The pharmaceutical composition according to item 71, wherein the integrase strand transfer inhibitors (INSTIs) are selected from the group consisting of dolutegravir, elvitegravir, raltegravir and bictegravir or mixtures thereof.
75) The pharmaceutical composition according to item 71, wherein the protease inhibitors (PIs) are selected from the group consisting of amprenavir, fosamprenavir, indinavir, lopinavir, nelfinavir, ritonavir, saquinavir, atazanavir, darunavir, tipranavir or mixtures thereof.
76) The pharmaceutical composition according to item 70, wherein the one or more additional active pharmaceutical ingredient is rilpivirine.
77) The pharmaceutical composition according to item 70, wherein the one or more additional active pharmaceutical ingredient is rilpivirine in form of its hydrochloride salt.
78) The pharmaceutical composition according to item 70, wherein the one or more additional active pharmaceutical ingredient is abacavir and/or lamivudine.
79) The pharmaceutical composition according to any one of items 66 to 78 which is an oral solid dosage form.
80) The pharmaceutical composition according to item 79, wherein the oral solid dosage form is a tablet or a capsule.
81) The pharmaceutical composition according to any one of items 66 to 80, wherein the crystalline form of cabotegravir sodium as defined in any one of items 1 to 21 is present in an amount selected from the group consisting of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg and 90 mg, calculated as cabotegravir.
82) The pharmaceutical composition according to item 81, wherein the crystalline form of cabotegravir sodium as defined in any one of items 1 to 21 or the crystalline form of cabotegravir sodium as defined in any one of items 88 to 97 is present in an amount of 30 mg, calculated as cabotegravir.
83) The pharmaceutical composition according to any one of items 66 to 82, which is administered once daily.
84) The pharmaceutical composition according to any one of items 66 to 83 for use as a medicament.

85) The pharmaceutical composition according to any one of items 66 to 83 for use in the treatment and/or prophylaxis of viral infections.

86) The pharmaceutical composition according to item 85, wherein the viral infection is caused by DNA viruses, RNA viruses, herpesviruses, retroviruses, hepadnaviruses, papillomavirus, hantavirus, adenoviruses and HIV.

87) The crystalline form of cabotegravir sodium as defined in any one of items 1 to 21 characterized by having a powder X-ray diffractogram not comprising a reflection at a 2-Theta angle of (5.4±0.2)° 2-Theta.

88) A crystalline form of cabotegravir sodium characterized by having a powder X-ray diffractogram comprising reflections at 2-Theta angles of (6.2±0.2)°, (17.3±0.2)° and (23.2±0.2)°, when measured at a temperature in the range of from 20 to 30° C. with Cu-Kalpha$_{1,2}$ radiation having a wavelength of 0.15419 nm.

89) A crystalline form of cabotegravir sodium characterized by having a powder X-ray diffractogram comprising reflections at 2-Theta angles of (6.2±0.2)°, (17.3±0.2)°, (21.7±0.2)° and (23.2±0.2)°, when measured at a temperature in the range of from 20 to 30° C. with Cu-Kalpha$_{1,2}$ radiation having a wavelength of 0.15419 nm.

90) A crystalline form of cabotegravir sodium characterized by having a powder X-ray diffractogram comprising reflections at 2-Theta angles of (6.2±0.2)°, (17.3±0.2)°, (21.7±0.2)°, (23.2±0.2)° and (25.1±0.2)°, when measured at a temperature in the range of from 20 to 30° C. with Cu-Kalpha$_{1,2}$ radiation having a wavelength of 0.15419 nm.

91) A crystalline form of cabotegravir sodium characterized by having a powder X-ray diffractogram comprising reflections at 2-Theta angles of (6.2±0.1)°, (17.3±0.1)°, and (23.2±0.1)°, when measured at a temperature in the range of from 20 to 30° C. with Cu-Kalpha$_{1,2}$ radiation having a wavelength of 0.15419 nm.

92) A crystalline form of cabotegravir sodium characterized by having a powder X-ray diffractogram comprising reflections at 2-Theta angles (6.2±0.1)°, (17.3±0.1)°, (21.7±0.1)° and (23.2±0.1)°, when measured at a temperature in the range of from 20 to 30° C. with Cu-Kalpha$_{1,2}$ radiation having a wavelength of 0.15419 nm.

93) A crystalline form of cabotegravir sodium characterized by having a powder X-ray diffractogram comprising reflections at 2-Theta angles of (6.2±0.1)°, (17.3±0.1)°, (21.7±0.1)°, (23.2±0.1)° and (25.1±0.1)°, when measured at a temperature in the range of from 20 to 30° C. with Cu-Kalpha$_{1,2}$ radiation having a wavelength of 0.15419 nm.

94) A crystalline form of cabotegravir sodium characterized by having a powder X-ray diffractogram comprising reflections at 2-Theta angles of (6.2±0.1)°, (9.1±0.1)°, (17.3±0.1)°, (21.7±0.1)°, (23.2±0.1)° and (25.1±0.1)°, when measured at a temperature in the range of from 20 to 30° C. with Cu-Kalpha$_{1,2}$ radiation having a wavelength of 0.15419 nm.

95) The crystalline form of cabotegravir sodium as defined in any one of items 88 to 94 characterized by having a powder X-ray diffractogram not comprising a reflection at a 2-Theta angle of (5.4±0.2)° 2-Theta.

96) The crystalline form of cabotegravir sodium as defined in any one of items 88 to 95 characterized by having a powder X-ray diffractogram not comprising a reflection at a 2-Theta angle of (6.8±0.2)° 2-Theta.

97) A crystalline form of cabotegravir sodium characterized by having a powder X-ray diffractogram essentially the same as shown in FIG. 5, when measured at a temperature in the range of from 20 to 30° C. with Cu-Kalpha$_{1,2}$ radiation having a wavelength of 0.15419 nm.

98) A composition comprising the crystalline form of cabotegravir sodium according to any one of items 88 to 97, which composition is essentially free of any other physical form of cabotegravir sodium.

99) A composition comprising the crystalline form of cabotegravir sodium according to any one of items 88 to 97, characterized by comprising at most 20 weight % of any other physical form of cabotegravir sodium, based on the weight of the composition.

100) A composition comprising the crystalline form of cabotegravir sodium according to any one of items 88 to 97, characterized by comprising at most 10 weight % of any other physical form of cabotegravir sodium, based on the weight of the composition.

101) A composition comprising the crystalline form of cabotegravir sodium according to any one of items 88 to 97, characterized by comprising at most 5 weight % of any other physical form of cabotegravir sodium, based on the weight of the composition.

102) A composition comprising the crystalline form of cabotegravir sodium according to any one of items 88 to 97, characterized by comprising at most 2 weight % of any other physical form of cabotegravir sodium, based on the weight of the composition.

103) A composition comprising the crystalline form of cabotegravir sodium according to any one of items 88 to 97, characterized by comprising at most 1 weight % of any other physical form of cabotegravir sodium, based on the weight of the composition.

104) The composition according to any one of items 98 to 103, wherein the any other physical form of cabotegravir sodium is Form A characterized by having a powder X-ray diffractogram comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.

105) The composition according to any one of items 98 to 103, wherein the any other physical form of cabotegravir sodium is amorphous.

106) A process for the preparation of the crystalline form of cabotegravir sodium as defined in any one of items 88 to 97 or the composition as defined in any one of items 98 to 105 comprising:
(i) providing a crystalline form of cabotegravir sodium (Form A) characterized by having a PXRD comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.
(ii) slurrying the crystalline form of cabotegravir sodium provided in step (i) in a solvent comprising methylisobutyl ketone, wherein the slurrying is for a time sufficient to effect transformation of cabotegravir sodium (Form A) to the crystalline form of cabotegravir sodium as defined in any one of items 88 to 97 or the composition as defined in any one of items 98 to 103.

107) The process according to any one of item 106, wherein cabotegravir sodium concentration of the suspension provided in step (ii) is in the range of from 5 to 80 g/L.

108) The process according to any one of items 106 to 107, wherein the cabotegravir sodium concentration of the suspension provided in step (ii) is in the range of from 5 to 50 g/L.

109) The process according to any one of items 106 to 108, wherein the cabotegravir sodium concentration of the suspension provided in step (ii) is in the range of from 5 to 25 g/L.

110) The process according to any one of items 106 to 108, wherein cabotegravir sodium concentration of the suspension provided in step (ii) is 10 g/L.

111) The process according to any one of items 106 to 110, wherein slurrying is performed at a temperature in the range of from 20 to 30° C.

112) The process according to any one of items 106 to 110, wherein slurrying is performed at a temperature in the range of from 40 to 80° C.

113) The process according to any one of items 106 to 110, wherein slurrying is performed at a temperature in the range of from 40 to 60° C.

114) The process according to any one of items 106 to 113, wherein the slurrying is performed for at least 24 hours.

115) The process according to item 114, wherein the slurrying is performed for at least 120 hours.

116) The process according to any one of items 106 to 115, further comprising step (iii) separating at least a part of the crystals obtained in step (ii) from the mother liquor.

117) The process according to item 116, wherein the crystals are separated from the mother liquor by filtration, centrifugation, decantation or solvent evaporation.

118) The process according to item 116, wherein the crystals are separated from the mother liquor by filtration or centrifugation.

119) The process according to item 116, wherein the crystals are separated from the mother liquor by filtration.

120) The process according to any one of items 106 to 119, further comprising step (iv) washing the isolated crystals obtained in step (iii).

121) The process according to item 120, wherein the crystals are washed with methylisobutyl ketone and/or water.

122) The process according to any one of items 98 to 121, further comprising step (v) drying the crystals obtained in any one of steps (ii) to (iv).

123) The process according to item 122, wherein drying is performed at a temperature of 150° C. or less.

124) The process according to item 122, wherein drying is performed at a temperature of 100° C. or less.

125) The process according to item 122, wherein drying is performed at a temperature of 60° C. or less.

126) The process according to item 122, wherein drying is performed at a temperature of 40° C. or less.

127) The process according to item 122, wherein drying is performed at a temperature in the range of from 20 to 30° C.

128) The process according to any one of items 122 to 127, wherein drying is performed for a period in the range of from 1 to 72 hours.

129) The process according to any one of items 122 to 127, wherein drying is performed for a period in the range of from 2 to 48 hours.

130) The process according to any one of items 122 to 127, wherein drying is performed for a period in the range of from 4 to 24 hours.

131) The process according to any one of items 122 to 127, wherein drying is performed for a period in the range of from 6 to 18 hours.

132) Use of the crystalline form of cabotegravir sodium as defined in any one of items 88 to 97 for the preparation of a pharmaceutical composition.

133) Use of the composition as defined in any one of items 98 to 103 for the preparation of a pharmaceutical composition.

134) The use according to any one of items 132 to 133, wherein the pharmaceutical composition is prepared by a wet or dry processing method.

135) The use according to item 134, wherein the wet processing method comprises wet granulation.

136) The use according to item 134, wherein the dry processing method comprises dry granulation or dry compaction.

137) A pharmaceutical composition comprising the crystalline form of cabotegravir sodium as defined in any one of items 88 to 97 or the composition as defined in any one of items 98 to 103 and at least one pharmaceutically acceptable excipient.

Definitions

The term "cabotegravir" as used herein refers to (3S,11aR)-N-[2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide according to Formula (I) disclosed herein above.

The term "cabotegravir sodium" as used herein refers to the sodium salt of cabotegravir, having a chemical structure, wherein about one mol of cabotegravir is associated with one mol of sodium via ionic interaction of deprotonated cabotegravir with $Na^+$. Cabotegravir sodium can be represented by the chemical structure according to Formula (II) herein after.

The term "cabotegravir sodium Form A" as used herein, refers to the crystalline form of cabotegravir sodium, which is for example inherently disclosed in Example Z-9 of WO 2006/116764 A1, Example Ae of WO 2010/068253 A1 and Example 17 of WO 2015/177537 A1. Form A of cabotegravir sodium can be characterized by having a powder X-ray diffractogram comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Typically, standard conditions can additionally mean a measurement under 20-80% relative humidity, preferably 30-70% relative humidity, more preferably 40-60% relative humidity and most preferably 50% relative humidity.

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

As used herein, the term "amorphous" refers to a solid form of a compound that is not crystalline. An amorphous compound possesses no long-range order and does not display a definitive X-ray diffraction pattern with reflections.

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-theta. Thus, a reflection that usually appears at 6.8° 2-Theta for example can appear between 6.6° and 7.0° 2-theta, preferably between 6.7 and 6.9° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

As used herein, the term "substantially free of any other physical form" with reference to a composition comprising a particular physical form of cabotegravir sodium means that the composition includes at most 20%, preferably at most 10%, more preferably at most 5%, even more preferably at most 2% and most preferably at most 1% by weight of any other physical form of cabotegravir sodium, based on the weight of the composition.

The term "physical form" as used herein refers to any crystalline and/or amorphous phase of a compound.

The terms "anhydrous form" or "anhydrate" as used herein refer to a crystalline solid where no water is incorporated into the crystal structure. Anhydrous forms may still contain residual water, which is not part of the crystal structure but may be adsorbed on the surface or absorbed in disordered regions of the crystal. Typically, an anhydrous form does not contain more than 1.0 w-%, preferably not more than 0.5 w-% and most preferably not more than 0.1 w-% of water, based on the weight of the crystalline form. The water content can be determined by Karl-Fischer Coulometry and/or by thermogravimetric analysis (TGA), e.g. by determining the weight loss in the range of from 25 to 200° C. at a heating rate of 10 K/min.

The term "non-solvated" as used herein, when talking about a crystalline solid indicates that no organic solvent is incorporated into the crystal structure. Non-solvated forms may still contain residual organic solvents, which are not part of the crystal structure but may be adsorbed on the surface or absorbed in disordered regions of the crystal. Typically, a non-solvated form does not contain more than 1.0 w-%, preferably not more than 0.5 w-%, and most preferably not more than 0.1 w-% of organic solvents, based on the weight of the crystalline form. The organic solvent content can be determined by thermogravimetric analysis (TGA), e.g. by determining the weight loss in the range of from 25 to 200° C. at a heating rate of 10 K/min.

Crystalline forms of cabotegravir sodium may be referred to herein as being characterized by a powder X-ray diffractogram "as shown in" a figure. The person skilled in the art understands that factors such as variations in instrument type, response and variations in sample directionality, sample concentration, sample purity, sample history and sample preparation may lead to variations, for example relating to the exact reflection positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "mother liquor" refers to the solution remaining after crystallization of a solid from said solution.

A "predetermined amount" as used herein with regard to cabotegravir sodium refers to the initial amount of cabotegravir sodium used for the preparation of a pharmaceutical composition having a desired dosage strength of cabotegravir.

The term "effective amount" as used herein with regard to cabotegravir sodium encompasses an amount of cabotegravir sodium, which causes the desired therapeutic and/or prophylactic effect.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

DETAILED DESCRIPTION OF THE INVENTION

Figure 1:
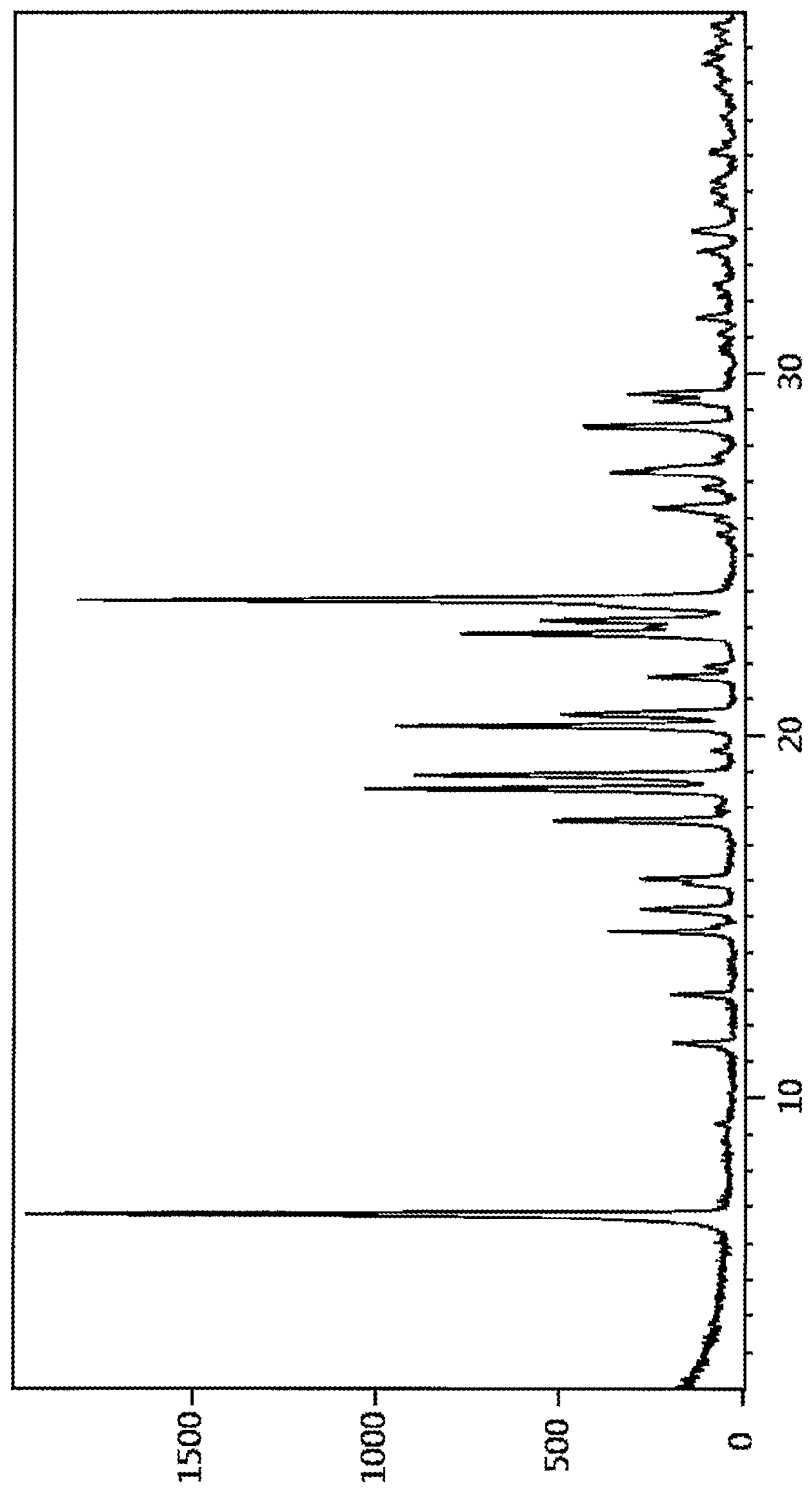
FIG. 1: illustrates a representative powder X-ray diffractogram of cabotegravir sodium Form B of the present invention. The x-axis shows the scattering angle in ° 2-Theta, the y-axis shows the intensity of the scattered X-ray beam in counts of detected photons.

The present invention provides novel crystalline forms of cabotegravir sodium, herein also referred to as "Form B" and "Form C".

The present inventors have surprisingly found that both Form B and Form C of the present invention are thermodynamically more stable than prior art Form A, at least at room temperature and elevated temperatures in the presence of particular organic solvents. The provision of a thermodynamically stable modification of cabotegravir sodium is highly desirable due to the fact that the risk of phase transitions, which may occur during manufacture and/or storage of a drug product, such as polymorphic conversions and/or amorphization, is minimized. Such transitions can in general have serious consequences for the pharmaceutical product with regard to safety and efficacy. Hence, Form B and Form C of the present invention are favored solid forms of cabotegravir sodium, to be used for the preparation of a pharmaceutical drug product. This is because the usage of Form B or Form C ensures a reliable safety and efficacy profile of a drug product containing Form B or Form C during the whole shelf-life of the product.

Cabotegravir sodium can be represented by the following chemical structure according to Formula (II)

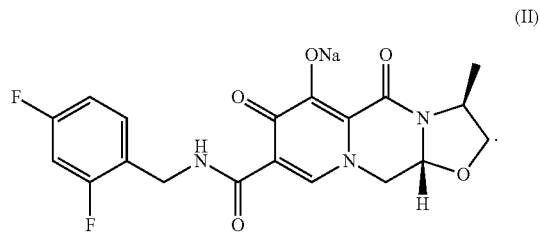

Cabotegravir sodium can be characterized by a molar ratio of cabotegravir and sodium preferably in the range of from 1.0:0.7 to 1.0:1.3, more preferably in the range of from 1.0:0.8 to 1.0:1.2, even more preferably in the range of from 1.0:0.9 to 1.0:1.1 and in particular the molar ratio is 1.0:1.0.

In one aspect, the present invention relates to a crystalline form of cabotegravir sodium, designated "Form B".

Cabotegravir sodium Form B of the present invention may be characterized by any one of the following embodiments or by combining two or more of the following embodiments.

Hence, the present invention relates to a crystalline form of cabotegravir sodium (Form B) which can be characterized by having a powder X-ray diffractogram comprising reflections at 2-Theta angles of:
(6.8±0.2)°, (18.5±0.2)° and (23.7±0.2)°; or
(6.8±0.2)°, (18.5±0.2)°, (20.3±0.2)° and (23.7±0.2)°; or
(6.8±0.2)°, (18.5±0.2)°, (18.9±0.2)°, (20.3±0.2)° and (23.7±0.2)°; or
(6.8±0.2)°, (18.5±0.2)°, (18.9±0.2)°, (20.3±0.2)°, (22.8±0.2)° and (23.7±0.2)°; or
(6.8±0.2)°, (18.5±0.2)°, (18.9±0.2)°, (20.3±0.2)°, (22.8±0.2)°, (23.2±0.2)° and (23.7±0.2)°; or
(6.8±0.2)°, (17.7±0.2)°, (18.5±0.2)°, (18.9±0.2)°, (20.3±0.2)°, (22.8±0.2)°, (23.2±0.2)° and (23.7±0.2)°; or
(6.8±0.2)°, (17.7±0.2)°, (18.5±0.2)°, (18.9±0.2)°, (20.3±0.2)°, (20.6±0.2)°, (22.8±0.2)°, (23.2±0.2)° and (23.7±0.2)°; or
(6.8±0.2)°, (17.7±0.2)°, (18.5±0.2)°, (18.9±0.2)°, (20.3±0.2)°, (20.6±0.2)°, (22.8±0.2)°, (23.2±0.2)°, (23.7±0.2)° and (28.6±0.2)°; or
(6.8±0.2)°, (14.6±0.2)°, (17.7±0.2)°, (18.5±0.2)°, (18.9±0.2)°, (20.3±0.2)°, (20.6±0.2)°, (22.8±0.2)°, (23.2±0.2)°, (23.7±0.2)° and (28.6±0.2)°; or
(6.8±0.2)°, (14.6±0.2)°, (17.7±0.2)°, (18.5±0.2)°, (18.9±0.2)°, (20.3±0.2)°, (20.6±0.2)°, (22.8±0.2)°, (23.2±0.2)°, (23.7±0.2)°, (27.3±0.2)° and (28.6±0.2)°;
when measured at a temperature in the range of from 20 to 30° C. with Cu-Kalpha$_{1,2}$ radiation having a wavelength of 0.15419 nm.

In another embodiment, the present invention relates to a crystalline form of cabotegravir sodium (Form B) which can be characterized by having a powder X-ray diffractogram comprising reflections at 2-Theta angles of:
(6.8±0.1)°, (18.5±0.1)° and (23.7±0.1)°; or
(6.8±0.1)°, (18.5±0.1)°, (20.3±0.1)° and (23.7±0.1)°; or
(6.8±0.1)°, (18.5±0.1)°, (18.9±0.1)°, (20.3±0.1)° and (23.7±0.1)°; or
(6.8±0.1)°, (18.5±0.1)°, (18.9±0.1)°, (20.3±0.1)°, (22.8±0.1)° and (23.7±0.1)°; or
(6.8±0.1)°, (18.5±0.1)°, (18.9±0.1)°, (20.3±0.1)°, (22.8±0.1)°, (23.2±0.1)° and (23.7±0.1)°; or (6.8±0.1)°, (17.7±0.1)°, (18.5±0.1)°, (18.9±0.1)°, (20.3±0.1)°, (22.8±0.1)°, (23.2±0.1)° and (23.7±0.1)°; or
(6.8±0.1)°, (17.7±0.1)°, (18.5±0.1)°, (18.9±0.1)°, (20.3±0.1)°, (20.6±0.1)°, (22.8±0.1)°, (23.2±0.1)° and (23.7±0.1)°; or
(6.8±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)° and (28.6±0.1)°; or
(6.8±0.1)°, (14.6±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)° and (28.6±0.1)°; or
(6.8±0.1)°, (14.6±0.1)°, (17.7±0.1)°, (18.5±0.1)°, (18.9±0.1)°, (20.3±0.1)°, (20.6±0.1)°, (22.8±0.1)°, (23.2±0.1)°, (23.7±0.1)°, (27.3±0.1)° and (28.6±0.1)°;
when measured at a temperature in the range of from 20 to 30° C. with Cu-Kalpha$_{1,2}$ radiation having a wavelength of 0.15419 nm.

In yet another embodiment, the present invention relates to a crystalline form of cabotegravir sodium (Form B) characterized by having a powder X-ray diffractogram essentially the same as shown in FIG. 1 of the present invention, when measured at a temperature in the range of from 20 to 30° C. with Cu-Kalpha$_{1,2}$ radiation having a wavelength of 0.15419 nm.

Figure 3:
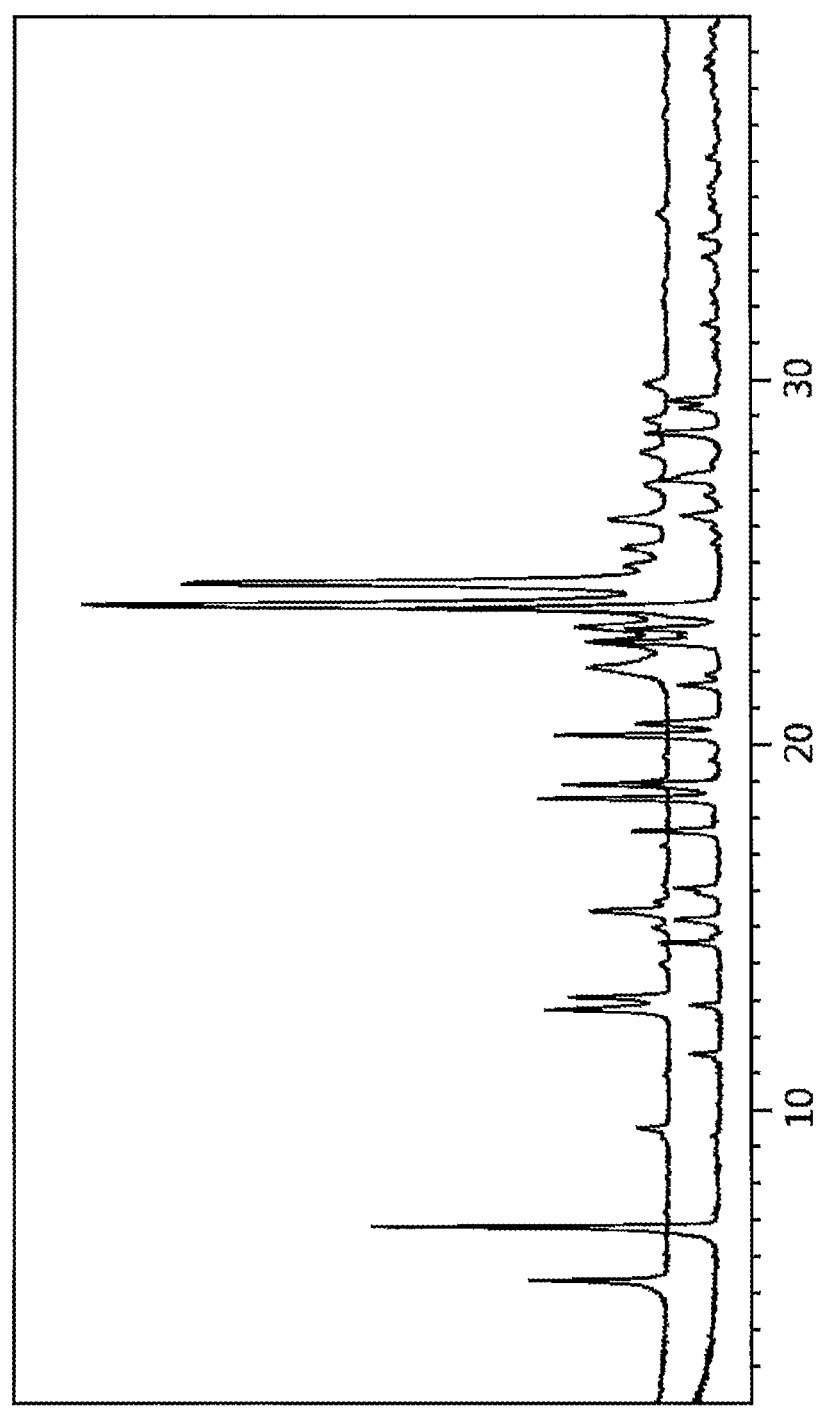
FIG. 3: illustrates a comparison of a representative powder X-ray diffractogram of crystalline Form B of cabotegravir sodium of the present invention (bottom) and a representative powder X-ray diffractogram of Form A of cabotegravir sodium prepared according to Reference Example 1 herein (top). The x-axis shows the scattering angle in ° 2-Theta. The powder X-ray diffractogram of Form A was shifted along the y-axis to separate the diffractograms for clarity. The y-axis is therefore arbitrary and was not labeled.
Figure 4:
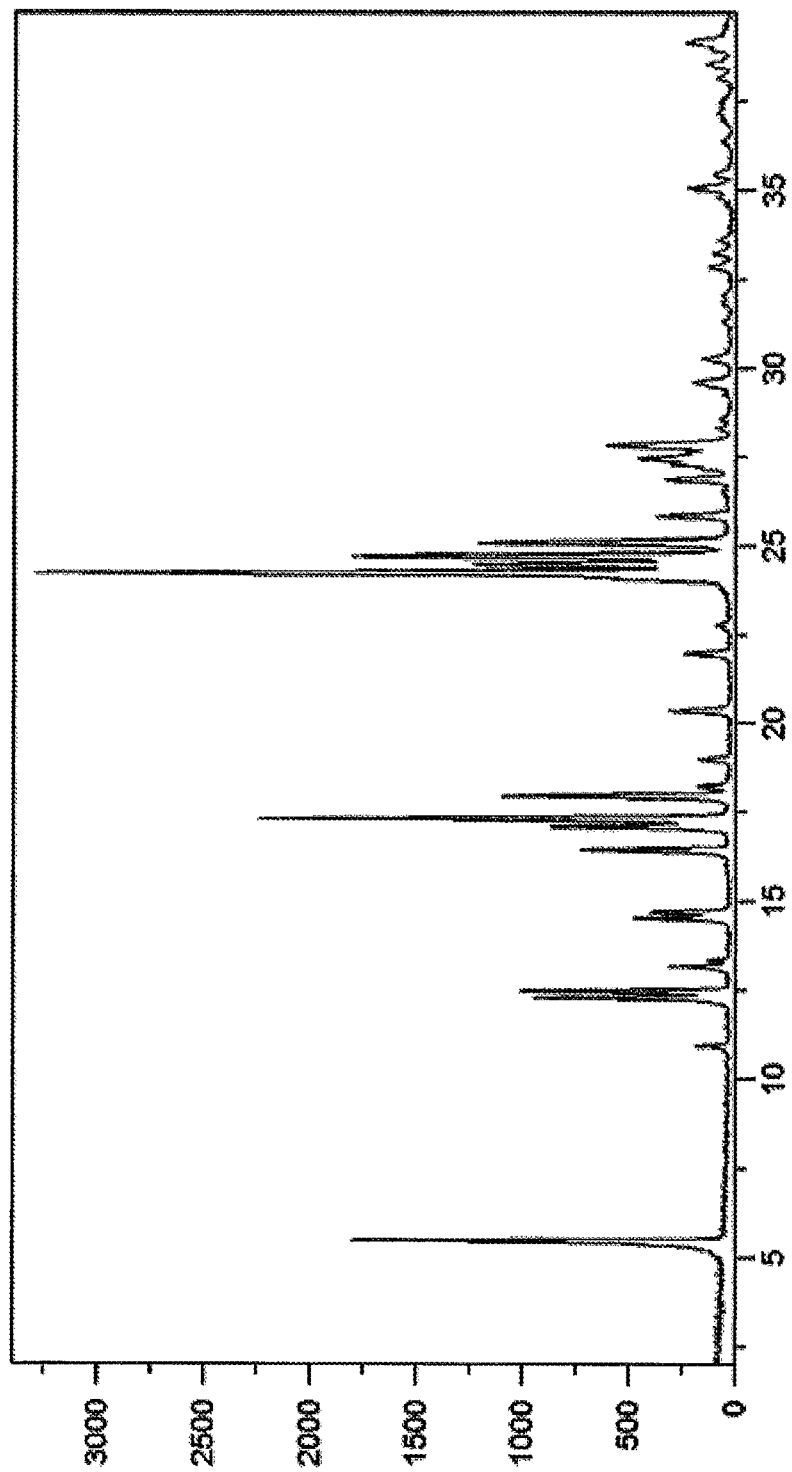
FIG. 4: illustrates a representative powder X-ray diffractogram of crystalline cabotegravir prepared according to Example D of WO 2011/119566 A1. The x-axis shows the scattering angle in ° 2-Theta, the y-axis shows the intensity of the scattered X-ray beam in counts of detected photons.

The powder X-ray diffractogram of cabotegravir sodium Form B of the present invention can be clearly distinguished from the one of prior art Form A (see also the overlay displayed in FIG. 3 herein). Form B shows for example a reflection at (6.8±0.2)° 2-Theta, whereas Form A shows no reflection in the same range. On the other hand, Form B shows no reflection at (5.4±0.2)° 2-Theta, whereas Form A possesses a characteristic reflection in this range. Thus, the crystalline form B of cabotegravir sodium can also be characterized by having a powder X-ray diffractogram as described above, but not comprising a reflection at a 2-Theta angle of (5.4±0.2)° 2-Theta.

Figure 7:
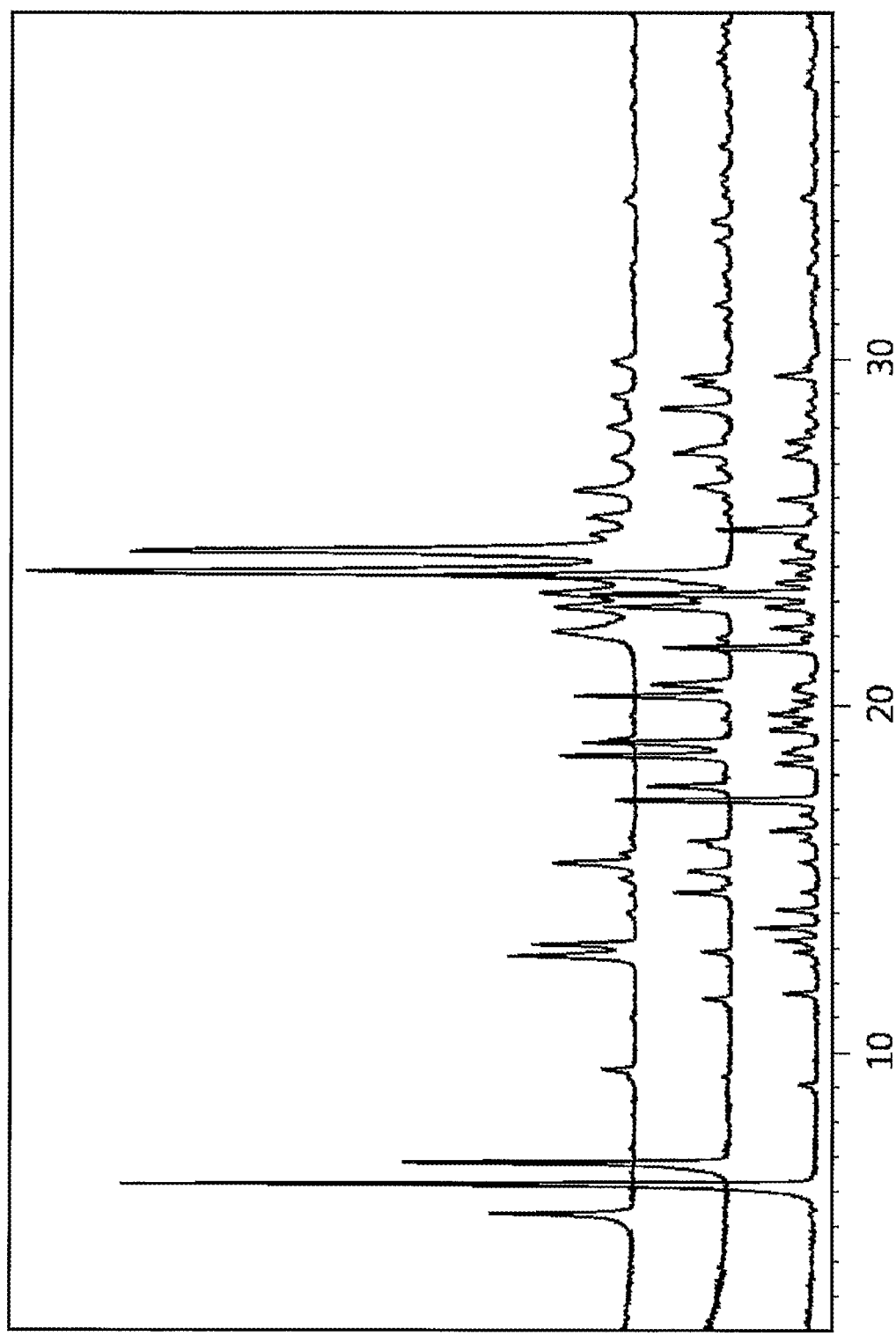
FIG. 7: illustrates a comparison of a representative powder X-ray diffractogram of crystalline Form C of cabotegravir sodium of the present invention (bottom), a representative powder X-ray diffractogram of crystalline Form B of cabotegravir sodium of the present invention (middle) and a representative powder X-ray diffractogram of Form A of cabotegravir sodium prepared according to Reference Example 1 herein (top). The x-axis shows the scattering angle in ° 2-Theta. The powder X-ray diffractograms of Form A and Form B were shifted along the y-axis to separate the diffractograms for clarity. The y-axis is therefore arbitrary and was not labeled.

The powder X-ray diffractogram of cabotegravir sodium Form B of the present invention can also be clearly distinguished from the one of Form C of the present invention (see also the overlay displayed in FIG. 7 herein). As already mentioned above, Form B shows a reflection at (6.8±0.2)° 2-Theta, whereas Form C shows no reflection in the same range. On the other hand, Form B shows no reflection at (6.2±0.2)° 2-Theta, whereas Form C possesses a characteristic reflection in this range. Thus, the crystalline form B of cabotegravir sodium can also be characterized by having a powder X-ray diffractogram as described above, but not comprising a reflection at a 2-Theta angle of (6.2±0.2)° 2-Theta. The crystalline form B of cabotegravir sodium can also be characterized by having a powder X-ray diffractogram as described above, but not comprising a reflection at 2-Theta angles of (5.4±0.2)° and (6.2±0.2)° 2-Theta. In one aspect, the present invention relates to a composition comprising Form B of cabotegravir sodium of the present invention, which is essentially free of any other physical forms of cabotegravir sodium. For example, a composition comprising Form B of cabotegravir sodium of the present invention comprises at most 20 weight %, preferably at most 10 weight %, more preferably at most 5 weight %, even more preferably at most 2 weight % and most preferably at most 1 weight % of any other physical form of cabotegravir sodium, based on the weight of the composition. Preferably, the any other physical form of cabotegravir sodium is Form A as defined herein, or it is Form C as defined herein or it is amorphous cabotegravir sodium. More preferably, the composition comprising Form B of cabotegravir sodium comprises at most 2 weight % of cabotegravir sodium Form A as defined herein, cabotegravir sodium Form C as defined herein and amorphous cabotegravir sodium combined.

In another aspect, the present invention relates to a process for the preparation of crystalline Form B of cabotegravir sodium of the present invention or the composition comprising Form B of cabotegravir sodium as defined above comprising:
(i) providing a crystalline form of cabotegravir sodium (Form A) characterized by having a PXRD comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.
(ii) slurrying the crystalline form of cabotegravir sodium (Form A) provided in step (i) in a solvent selected from the group consisting of cyclic ethers, C$_3$-C$_4$ ketones and methyl acetate or mixtures thereof, wherein the slurrying is for a time sufficient to effect transformation of cabotegravir sodium (Form A) to crystalline Form B of cabotegravir sodium of the present invention;
(iii) optionally separating at least a part of the crystals obtained in step (ii) from their mother liquor;
(iv) optionally washing the isolated crystals obtained in step (iii);
(v) optionally drying the crystals obtained in any one of steps (ii) to (iv);

Cabotegravir sodium Form A, which is applied as starting material in the above described process can be prepared according to the procedures disclosed in Example Z-1 of WO 2006/116764 A1, Example Ae of WO 2010/068253 A, Example 17 of WO 2015/177537 A1 or according to the teaching of J. Med. Chem. 2013, 56, 5901-5916.

The solvent-mediated transformation of cabotegravir sodium Form A to cabotegravir sodium Form B may be accomplished by applying conditions as defined hereinafter.

A suitable solvent, which may be used in step (ii) of the above described process may be selected from the group consisting of cyclic ethers, C$_3$-C$_4$ ketones and methyl acetate or mixtures thereof. In a preferred embodiment, the cyclic ethers are selected from tetrahydrofuran and 1,4-dioxane and the C$_3$-C$_4$ ketones are selected from acetone and 2-butanone. The solvent or solvent mixture may comprise additional organic solvents and/or water. However, most preferably the only solvent present in the slurry is selected from the group consisting of tetrahydrofuran, 1,4-dioxane, acetone, 2-butanone and methyl acetate.

The cabotegravir sodium concentration of the suspension is preferably in the range of from about 5 to 80 g/L, more preferably from about 5 to 50 g/L and most preferably from about 5 to 25 g/L, for example the concentration is about 10 g/L.

Preferably, slurrying is performed at room temperature but depending on the applied concentration may also be conducted at elevated temperature for example at a temperature in the range of from about 40 to 80° C., preferably from about 40 to 60° C.

Slurrying encompasses any kind of movement of the solid material suspended in the solvent caused by, but not limited to e.g. agitation, stirring, mixing, shaking, vibration, sonication, wet milling and the like.

Slurrying is conducted for a time sufficient that at least a substantial part, preferably all of Form A has converted to Form B. Preferably slurrying is performed for a period in the range of several hours to several days. Slurrying may for example be performed for a period in the range of from 6 hours to 14 days or longer. The skilled person may monitor the conversion of cabotegravir sodium Form A to Form B by withdrawing samples from the slurry and analyzing the samples by powder X-ray diffraction.

Once cabotegravir sodium Form B is obtained or preferably obtained in essentially pure form, at least a part of the crystals is optionally separated from its mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with a suitable solvent, for example an organic solvent and/or water. Suitable organic solvents comprise, but are not limited to tetrahydrofuran, 1,4-dioxane, acetone, 2-butanone and methyl acetate. Most preferably, the solvent applied in step (ii) of the above defined process is also used for washing.

The obtained crystals may then optionally be dried. Drying may be performed at a temperature of about 150° C. or less, preferably of about 100° C. or less, more preferably of about 60° C. or less and most preferably of about 40° C. or less. Typically, drying is performed at room temperature. Drying may be performed for a period in the range of from about 1 to 72 hours, preferably from 2 to 48 hours, more preferably from 4 to 24 hours and most preferably from 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 20 mbar or less.

In a further aspect, the present invention relates to a crystalline form of cabotegravir sodium, designated "Form C".

Cabotegravir sodium Form C of the present invention may be characterized by any one of the following embodiments or by combining two or more of the following embodiments.

Hence, the present invention relates to a crystalline form of cabotegravir sodium (Form C) which can be characterized by having a powder X-ray diffractogram comprising reflections at 2-Theta angles of:
(6.2±0.2)°, (17.3±0.2)° and (23.2±0.2)°; or
(6.2±0.2)°, (17.3±0.2)°, (21.7±0.2)° and (23.2±0.2)°; or
(6.2±0.2)°, (17.3±0.2)°, (21.7±0.2)°, (23.2±0.2)° and (25.1±0.2)°; or
(6.2±0.2)°, (9.1±0.2)°, (17.3±0.2)°, (21.7±0.2)°, (23.2±0.2)° and (25.1±0.2)°; or
(6.2±0.2)°, (9.1±0.2)°, (11.7±0.2)°, (17.3±0.2)°, (21.7±0.2)°, (23.2±0.2)° and (25.1±0.2)°; or
(6.2±0.2)°, (9.1±0.2)°, (11.7±0.2)°, (13.6±0.2)°, (17.3±0.2)°, (21.7±0.2)°, (23.2±0.2)° and (25.1±0.2)°;
when measured at a temperature in the range of from 20 to 30° C. with Cu-Kalpha$_{1,2}$ radiation having a wavelength of 0.15419 nm.

In another embodiment, the present invention relates to a crystalline form of cabotegravir sodium (Form C) which can be characterized by having a powder X-ray diffractogram comprising reflections at 2-Theta angles of:
(6.2±0.1)°, (17.3±0.1)° and (23.2±0.1)°; or
(6.2±0.1)°, (17.3±0.1)°, (21.7±0.1)° and (23.2±0.1)°; or
(6.2±0.1)°, (17.3±0.1)°, (21.7±0.1)°, (23.2±0.1)° and (25.1±0.1)°; or
(6.2±0.1)°, (9.1±0.1)°, (17.3±0.1)°, (21.7±0.1)°, (23.2±0.1)° and (25.1±0.1)°; or
(6.2±0.1)°, (9.1±0.1)°, (11.7±0.1)°, (17.3±0.1)°, (21.7±0.1)°, (23.2±0.1)° and (25.1±0.1)°; or
(6.2±0.1)° (9.1±0.1)°, (11.7±0.1)°, (13.6±0.1)°, (17.3±0.1)°, (21.7±0.1)°, (23.2±0.1)° and (25.1±0.1)°;
when measured at a temperature in the range of from 20 to 30° C. with Cu-Kalpha$_{1,2}$ radiation having a wavelength of 0.15419 nm.

Figure 5:
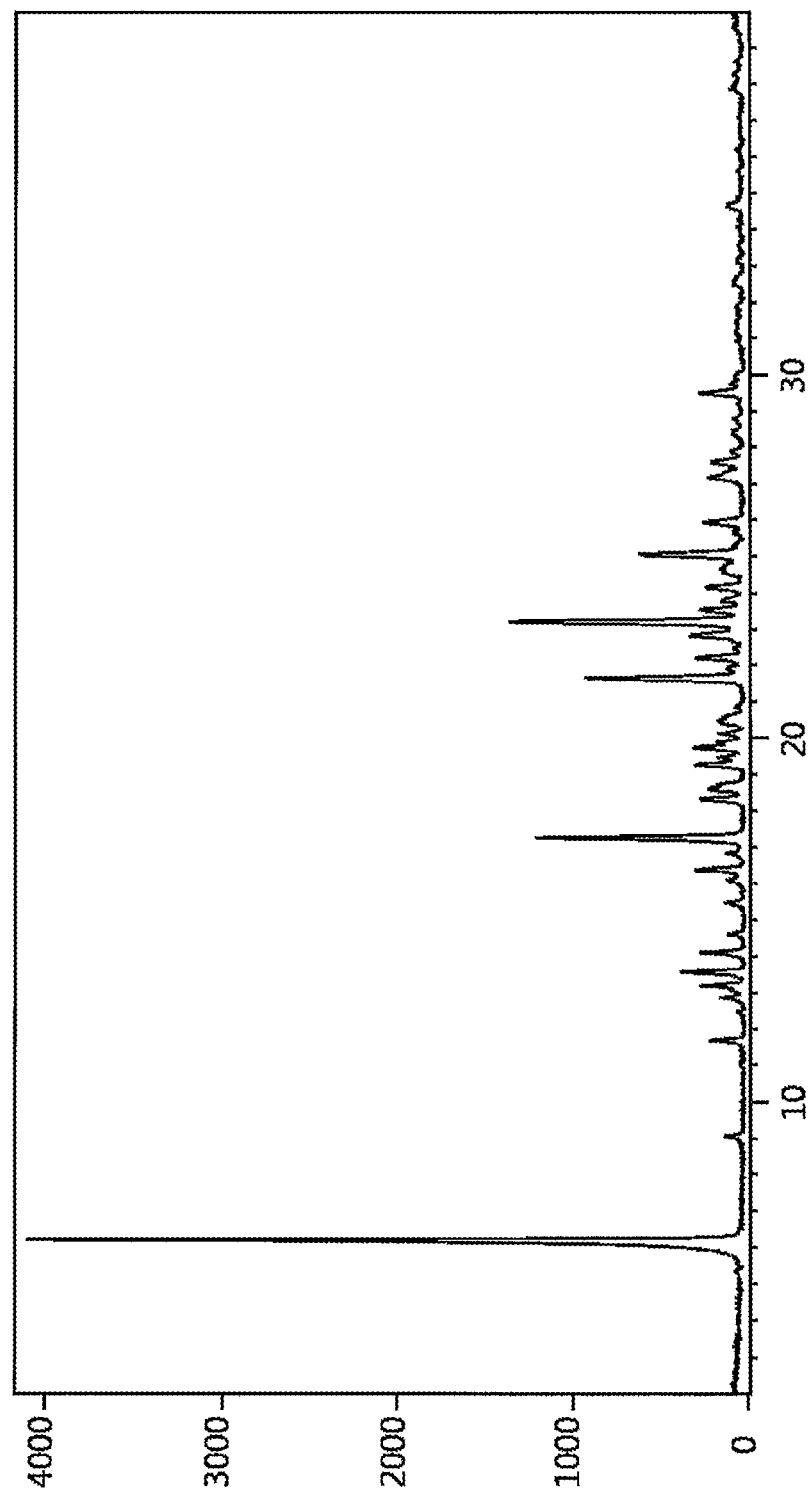
FIG. 5: illustrates a representative powder X-ray diffractogram of cabotegravir sodium Form C of the present invention. The x-axis shows the scattering angle in ° 2-Theta, the y-axis shows the intensity of the scattered X-ray beam in counts of detected photons.

In yet another embodiment, the present invention relates to a crystalline form of cabotegravir sodium (Form C) characterized by having a powder X-ray diffractogram essentially the same as shown in FIG. 5 of the present invention, when measured at a temperature in the range of from 20 to 30° C. with Cu-Kalpha$_{1,2}$ radiation having a wavelength of 0.15419 nm.

Figure 6:
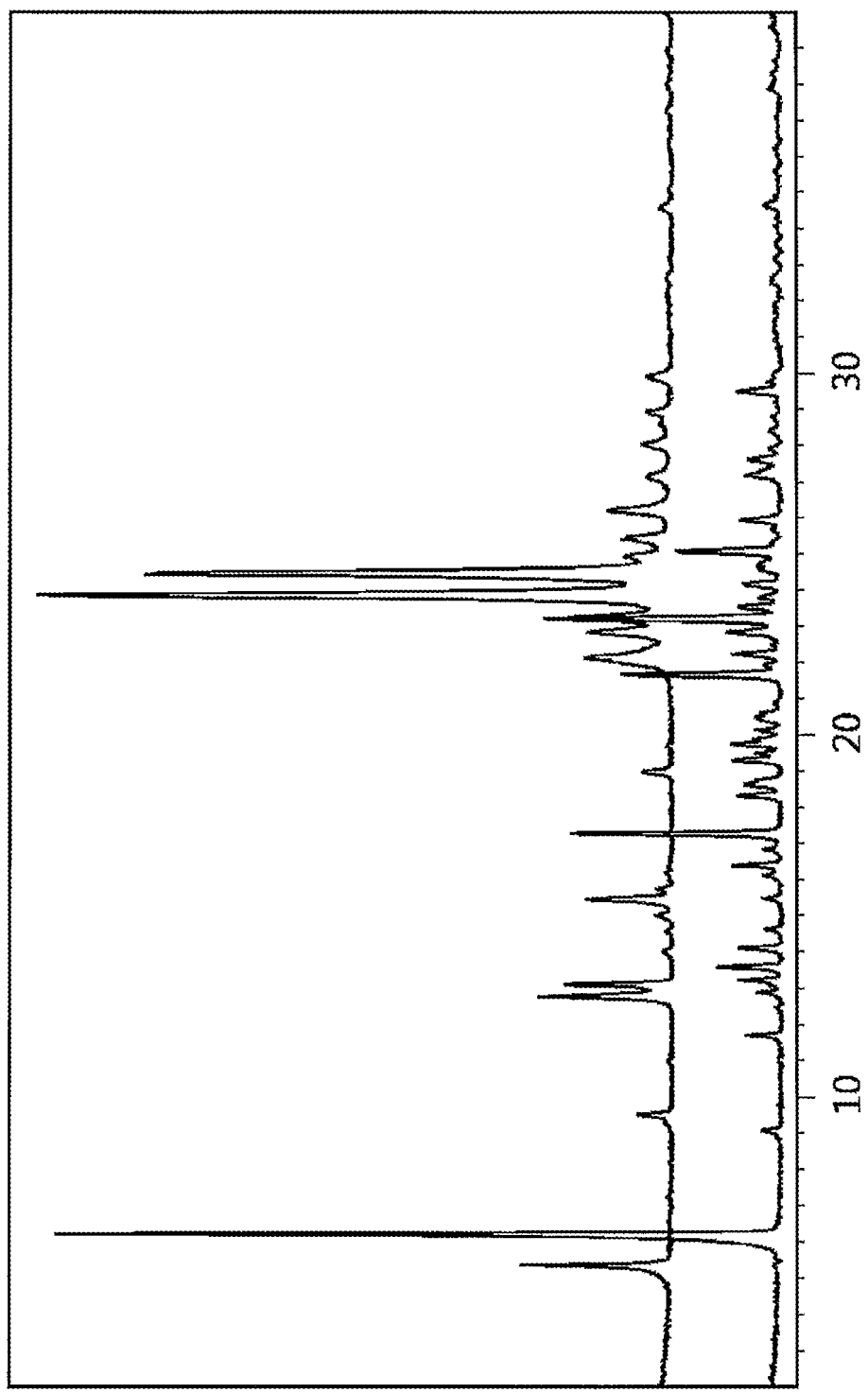
FIG. 6: illustrates a comparison of a representative powder X-ray diffractogram of crystalline Form C of cabotegravir sodium of the present invention (bottom) and a representative powder X-ray diffractogram of Form A of cabotegravir sodium prepared according to Reference Example 1 herein (top). The x-axis shows the scattering angle in ° 2-Theta. The powder X-ray diffractogram of Form A was shifted along the y-axis to separate the diffractograms for clarity. The y-axis is therefore arbitrary and was not labeled.

The powder X-ray diffractogram of cabotegravir sodium Form C of the present invention can be clearly distinguished from the one of prior art Form A (see also the overlay displayed in FIG. 6 herein). Form C shows for example a reflection at (6.2±0.2)° 2-Theta, whereas Form A shows no reflection in the same range. On the other hand, Form C shows no reflection at (5.4±0.2)° 2-Theta, whereas Form A possesses a characteristic reflection in this range. Thus, the crystalline form C of cabotegravir sodium can also be characterized by having a powder X-ray diffractogram as described above, but not comprising a reflection at a 2-Theta angle of (5.4±0.2)° 2-Theta.

As already mentioned above, the powder X-ray diffractogram of cabotegravir sodium Form C of the present invention can also be clearly distinguished from the one of Form B of the present invention (see also the overlay displayed in FIG. 7 herein). Form C shows for example a reflection at (6.2±0.2)° 2-Theta, whereas Form B shows no reflection in the same range. On the other hand, Form C shows no reflection at (6.8±0.2)° 2-Theta, whereas Form B possesses a characteristic reflection in this range. Thus, the crystalline form C of cabotegravir sodium can also be characterized by having a powder X-ray diffractogram as described above, but not comprising a reflection at a 2-Theta angle of (6.8±0.2)° 2-Theta.

The crystalline form C of cabotegravir sodium can also be characterized by having a powder X-ray diffractogram as described above, but not comprising a reflection at 2-Theta angles of (5.4±0.2)° and (6.8±0.2)° 2-Theta.

In a further aspect, the present invention relates to a composition comprising Form C of cabotegravir sodium of the present invention, which is essentially free of any other physical forms of cabotegravir sodium. For example, a composition comprising Form C of cabotegravir sodium of the present invention comprises at most 20 weight %, preferably at most 10 weight %, more preferably at most 5 weight %, even more preferably at most 2 weight % and most preferably at most 1 weight % of any other physical form of cabotegravir sodium, based on the weight of the composition. Preferably, the any other physical form of cabotegravir sodium is Form A as defined herein, or it is Form B as defined herein or it is amorphous cabotegravir sodium. More preferably, the composition comprising Form C of cabotegravir sodium comprises at most 2 weight % of cabotegravir sodium Form A as defined herein, cabotegravir sodium Form B as defined herein and amorphous cabotegravir sodium combined.

In another aspect, the present invention relates to a process for the preparation of crystalline Form C of cabotegravir sodium of the present invention or the composition comprising Form C of cabotegravir sodium as defined above comprising:

(i) providing a crystalline form of cabotegravir sodium (Form A) characterized by having a PXRD comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.

(ii) slurrying the crystalline form of cabotegravir sodium (Form A) provided in step (i) in methylisobutyl ketone, wherein the slurrying is for a time sufficient to effect transformation of cabotegravir sodium (Form A) to crystalline Form C of cabotegravir sodium of the present invention and wherein the slurrying is stopped before the obtained crystalline Form C further transforms to crystalline Form B of cabotegravir sodium as defined herein above;

(iii) optionally separating at least a part of the crystals obtained in step (ii) from their mother liquor;

(iv) optionally washing the isolated crystals obtained in step (iii);

(v) optionally drying the crystals obtained in any one of steps (ii) to (iv);

Cabotegravir sodium Form A, which is applied as starting material in the above described process can be prepared according to the procedures disclosed in Example Z-1 of WO 2006/116764 A1, Example Ae of WO 2010/068253 A, Example 17 of WO 2015/177537 A1 or according to the teaching of J. Med. Chem. 2013, 56, 5901-5916.

The solvent-mediated transformation of cabotegravir sodium Form A to cabotegravir sodium Form C may be accomplished by applying conditions as defined hereinafter.

A suitable solvent, which may be used in step (ii) of the above described is methylisobutyl ketone. Besides methylisobutyl ketone the solvent may comprise additional organic solvents and/or water. However, most preferably methylisobutyl ketone is the only solvent present in the slurry.

The cabotegravir sodium concentration of the suspension is preferably in the range of from about 5 to 80 g/L, more preferably from about 5 to 50 g/L and most preferably from about 5 to 25 g/L, for example the concentration is about 10 g/L.

Slurrying may be performed at room temperature but may also be conducted at elevated temperature. Preferably, slurrying is performed at a temperature in the range of from about 40 to 80° C., even more preferably from about 40 to 60° C.

Slurrying encompasses any kind of movement of the solid material suspended in the solvent caused by, but not limited to e.g. agitation, stirring, mixing, shaking, vibration, sonication, wet milling and the like.

Slurrying is conducted for a time sufficient that at least a substantial part, preferably all of Form A has converted to Form C and slurrying is stopped before Form C further converts to Form B. Depending on the applied temperature, slurrying is performed for a period in the range of several hours to several days, wherein the slurrying time decreases with increasing temperature For example, slurrying may be performed at a temperature of 60° C. for about 2 days or at room temperature for about 10 days. The skilled person may monitor the conversion of cabotegravir sodium Form A to Form B by withdrawing samples from the slurry and analyzing the samples by powder X-ray diffraction. Preferably, slurrying is stopped as soon as a substantial part, preferably all of Form A has converted to Form C in order to avoid further transformation to Form B.

Once cabotegravir sodium Form C is obtained or preferably obtained in essentially pure form, at least a part of the crystals may be separated from its mother liquor. Preferably, the crystals are separated from the mother liquor by any conventional method such as filtration, centrifugation, solvent evaporation or decantation, more preferably by filtration or centrifugation and most preferably by filtration.

Optionally, in a further step the isolated crystals are washed with a suitable solvent, for example an organic solvent and/or water. A suitable organic solvents is for example methylisobutyl ketone.

The obtained crystals may then optionally be dried. Drying may be performed at a temperature of about 150° C. or less, preferably of about 100° C. or less, more preferably of about 60° C. or less and most preferably of about 40° C. or less. Typically, drying is performed at room temperature. Drying may be performed for a period in the range of from about 1 to 72 hours, preferably from 2 to 48 hours, more preferably from 4 to 24 hours and most preferably from 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 20 mbar or less.

It was surprisingly found by the present inventors that prior art Form A of cabotegravir sodium undergoes a solvent-mediated phase transformation to a more stable modification, namely Form B of the present invention, when slurried for a sufficiently long time in the presence of a suitable organic solvent. This indicates that crystalline Form B of cabotegravir sodium is the thermodynamically more stable solid form at the tested conditions (see also Example 1 and Reference Example 1 herein).

In addition, it was found that prior art Form A of cabotegravir sodium undergoes a solvent-mediated phase transformation to another more stable modification, namely Form C of the present invention, when slurried for a sufficiently long time in the presence of methylisobutyl ketone, which indicates that Form C of cabotegravir sodium is the thermodynamically more stable form at these specific test conditions (see also Examples 2 and 3 herein).

The exact conditions used for the slurry experiments are described in more detail in Examples 1 to 3 herein. A summary of the performed slurry experiments is provided in Table 1 below:

TABLE 1

Overview of performed slurry experiments

| Starting Material | Solvent | Temperature | Result |
| --- | --- | --- | --- |
| Form A | acetone | room temperature | Form B |
| Form A | 2-butanone | room temperature | Form B |
| Form A | methyl acetate | room temperature | Form B |
| Form A | tetrahydrofuran | room temperature | Form B |
| Form A | 1,4-dioxane | room temperature | Form B |
| Form A | 2-butanone | 20° C. | Form B |
| Form A | 2-butanone | 40° C. | Form B |
| Form A | 2-butanone | 60° C. | Form B |
| Form A | 2-butanone | 80° C. | Form B |
| Form A | methylisobutyl ketone | room temperature | Form C |
| Form A | methylisobutyl ketone | 60° C. | Form C |
| Form A + Form B | 2-butanone | 20° C. | Form B |
| Form A + Form B | 2-butanone | 40° C. | Form B |
| Form A + Form B | 2-butanone | 60° C. | Form B |
| Form A + Form B | 2-butanone | 80° C. | Form B |

Under the given conditions Form A converted to Form B and Form C respectively, which indicates that both modifications of the present invention are thermodynamically more stable than prior art Form A, at least under the tested conditions. The competitive slurry experiments performed with equal amounts of Form A and Form B further confirm that Form B is thermodynamically more stable than Form A (see also Example 5 herein).

The thermodynamically most stable polymorphic form or at least a kinetically stable form is preferably used for drug product development, because metastable polymorphs may transform to a more stable one during pharmaceutical processing and/or upon storage. Such a phase change may cause formulation problems such as physical instability of the solid dosage form and changes in bioavailability. The usage of the thermodynamically most stable form or at least a kinetically stable form is highly appreciated since the risk of polymorphic conversions can usually be minimized, and consistent quality and efficacy of the drug product can be provided.

Hence, cabotegravir sodium Form B and Form C of the present invention are favored over Form A in order to ensure a safe and efficacious drug product for the patient.

Therefore, in a further aspect the present invention relates to the use of cabotegravir sodium Form B or Form C of the present invention as defined above for the preparation of a pharmaceutical composition.

The pharmaceutical composition of the present invention can be prepared by wet or dry processing methods. In certain embodiments the pharmaceutical composition is prepared by wet processing methods, such as, but not limited to, wet granulation methods. Suitable wet granulation methods comprise high-shear granulation or fluid-bed granulation. In another embodiment the pharmaceutical composition is prepared by dry processing methods, such as, but not limited to, direct compression or dry granulation methods. An example of dry granulation is roller compaction. The pharmaceutical composition obtained by dry or wet processing methods may be compressed into tablets, encapsulated or metered into sachets.

In a further aspect, the present invention relates to a pharmaceutical composition comprising cabotegravir sodium Form B or Form C as defined above, preferably in an effective and/or predetermined amount, and at least one pharmaceutically acceptable excipient and optionally one or more additional active pharmaceutical ingredient(s). Most preferably, the pharmaceutical composition of the present invention is an oral solid dosage form, such as a tablet or a capsule. Preferably, the pharmaceutical composition of the present invention is a tablet. In a preferred embodiment, the tablet is film-coated with a coating material containing polyvinyl alcohol (e.g. partially hydrolyzed), iron oxide (e.g. yellow), talc, and titanium dioxide.

The at least one pharmaceutically acceptable excipient, which is comprised in the pharmaceutical composition of the present invention, is preferably selected from the group consisting of carriers, fillers, diluents, lubricants, sweeteners, stabilizing agents, solubilizing agents, antioxidants and preservatives, flavouring agents, binders, colorants, osmotic agents, buffers, surfactants, disintegrants, granulating agents, coating materials and combinations thereof.

In a preferred embodiment, the at least one pharmaceutically acceptable excipient is selected from the group consisting of mannitol, microcrystalline cellulose, povidone, sodium starch glycolate and sodium stearyl fumarate. In a preferred embodiment, all of these pharmaceutically acceptable excipients are comprised by the pharmaceutical composition of the present invention.

In another preferred embodiment, the one or more additional active pharmaceutical ingredient(s) is/are selected from the group consisting of entry/fusion inhibitors, reverse transcriptase inhibitors (RTIs), integrase strand transfer inhibitors (INSTI), maturation inhibitors, protease inhibitors (PIs) or mixtures thereof. In a further preferred embodiment, the entry/fusion inhibitors are selected from the group consisting of enfuvirtide, maraviroc, vicriviroc, cenicriviroc and fostemsavir or mixtures thereof, the reverse transcriptase inhibitors (RTIs) are selected from the group consisting of abacavir, didanosine, emtricitabine, lamivudine, stavudine, zidovudine, amdoxovir, apricitabine, censavudine, elvucitabine, racivir, stampidine, zalcitabine, tenofovir disoproxil, tenofovir alafenamide, efavirenz, nevirapine, delavirdine, etravirine, rilpivirine, doravirine or mixtures thereof, the integrase strand transfer inhibitors (INSTI) are selected from the group consisting of dolutegravir, elvitegravir, raltegravir and bictegravir or mixtures thereof, the maturation inhibitor is bevirimat and the protease inhibitors (PIs) are selected from the group consisting of amprenavir, fosamprenavir, indinavir, lopinavir, nelfinavir, ritonavir, saquinavir, atazanavir, darunavir, tipranavir or mixtures thereof.

In a particular preferred embodiment, the one or more additional active pharmaceutical ingredient(s) is/are selected from the group consisting of rilpivirine and lamivudine, most preferably the one or more additional active pharmaceutical ingredient is rilpivirine e.g. in form of its hydrochloride salt.

Preferably, the present invention relates to a pharmaceutical composition as describe above, wherein the predetermined and/or effective amount of cabotegravir sodium is selected from the group consisting of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg and 90 mg calculated as cabotegravir. Most preferably, the invention relates to a pharmaceutical composition as describe above, wherein the predetermined and/or effective amount of cabotegravir sodium is 30 mg calculated as cabotegravir.

Preferably, the present invention relates to a pharmaceutical composition as described above, wherein the pharmaceutical composition is to be administered once-daily.

In a further aspect, the present invention relates to the pharmaceutical composition as described above for use as a medicament.

In yet another aspect, the present invention relates to the pharmaceutical composition as described above for use in the treatment or prophylaxis of viral infections caused by DNA viruses, RNA viruses, herpesviruses (e.g. CMV, HSV 1, HSV 2, VZV), retroviruses, hepadnaviruses (e.g. HBV), papillomavirus, hantavirus, adenoviruses and HIV.

In a particular embodiment, the present invention relates to the pharmaceutical composition as described above for use in the treatment or prophylaxis of HIV-1 infections.

In another aspect the present invention relates to the pharmaceutical composition as described above intended for the treatment of HIV-1 infections in combination with one or more additional active pharmaceutical ingredient(s) selected from the group consisting of entry/fusion inhibitors, reverse transcriptase inhibitors (RTIs), integrase strand transfer inhibitors (INSTI), maturation inhibitors, protease inhibitors (PIs) or mixtures thereof. In a further preferred embodiment, the entry/fusion inhibitors are selected from the group consisting of enfuvirtide, maraviroc, vicriviroc, cenicriviroc, ibalizumab and fostemsavir or mixtures thereof, the reverse transcriptase inhibitors (RTIs) are selected from the group consisting of abacavir, didanosine, emtricitabine, lamivudine, stavudine, zidovudine, amdoxovir, apricitabine, censavudine, elvucitabine, racivir, stampidine, zalcitabine, tenofovir disoproxil, tenofovir alafenamide, efavirenz, nevirapine, delavirdine, etravirine, rilpivirine, doravirine or mixtures thereof, the integrase strand transfer inhibitors (INSTI) are selected from the group consisting of dolutegravir, elvitegravir, raltegravir and bictegravir or mixtures thereof, the maturation inhibitor is bevirimat and the protease inhibitors (PIs) are selected from the group consisting of amprenavir, fosamprenavir, indinavir, lopinavir, nelfinavir, ritonavir, saquinavir, atazanavir, darunavir, tipranavir or mixtures thereof.

A treatment in combination with one or more additional active pharmaceutical ingredient(s) can mean the administration of a pharmaceutical dosage form comprising the cabotegravir sodium form B of the present invention and the one or more additional active pharmaceutical ingredient(s) in the same dosage form, for example as a fixed-dose combination.

Alternatively, a treatment in combination with one or more additional active pharmaceutical ingredient(s) can mean the administration of separate pharmaceutical dosage forms, one comprising the cabotegravir sodium form B of the present invention, and the other(s) comprising the one or more additional active pharmaceutical ingredient(s) in separate dosage form(s). Typically in such a combination treatment instructions are provided that the pharmaceutical dosage form comprising the cabotegravir sodium form B of the present invention is to be administered in combination with said separate dosage form(s) for the effective treatment of a viral invention, such as HIV-1 infection.

EXAMPLES

The following non-limiting examples are illustrative for the disclosure and are not to be construed as to be in any way limiting for the scope of the invention.

Example 1: Preparation of Cabotegravir Sodium Form B

Cabotegravir sodium Form A (approximately 50 mg, prepared according to Reference Example 1 herein) was suspended in an organic solvent (5 mL) according to Table 2 and vigorously stirred at room temperature using a magnetic stirrer. After 7 days, the solids were collected by filtration dried under vacuum (30 mbar) at room temperature for 20 hours and analyzed by PXRD. The results are displayed in Table 2.

TABLE 2

Overview equilibrium slurry experiments starting from cabotegravir sodium Form A

| Example | Solvent | Weighted sample | Result (PXRD) |
| --- | --- | --- | --- |
| 1.1 | acetone | 46 mg Form A | Form B |
| 1.2 | 2-butanone | 47 mg Form A | Form B |
| 1.3 | methyl acetate | 47 mg Form A | Form B |
| 1.4 | tetrahydrofuran | 46 mg Form A | Form B |
| 1.5 | 1,4-dioxane | 54 mg Form A | Form B |

PXRD was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40 s per step (255 channels) in the angular range of 2° to 40° 2-theta at ambient conditions. A typical precision of the 2-theta values is in the range of ±0.2° 2-Theta, preferably of ±0.1° 2-Theta. Thus, the diffraction peak of cabotegravir sodium Form B that appears for example at 6.8° 2-Theta can appear in the range of from 6.6 to 7.0° 2-Theta, preferably in the range of from 6.7 to 6.9° 2-Theta on most X-ray diffractometers under standard conditions.

A representative diffractogram of cabotegravir sodium Form B is displayed in FIG. 1 herein. The corresponding reflection list is provided in Table 3 below.

TABLE 3

PXRD reflections and corresponding relative intensities of cabotegravir sodium Form B in the range of from 2 to 30° 2-Theta; A typical precision of the 2-Theta values is in the range of ±0.2° 2-Theta, preferably of ±0.1° 2-Theta.

| Reflection position [° 2-Theta] | Relative intensity [%] |
| --- | --- |
| 6.8 | 100 |
| 11.5 | 9 |
| 12.9 | 9 |
| 14.6 | 18 |
| 15.3 | 11 |
| 15.9 | 6 |
| 16.1 | 13 |
| 17.7 | 25 |
| 18.5 | 54 |
| 18.9 | 46 |
| 20.3 | 49 |
| 20.6 | 23 |
| 21.6 | 11 |
| 22.8 | 39 |
| 23.2 | 26 |
| 23.7 | 92 |
| 26.3 | 11 |
| 27.3 | 18 |
| 27.4 | 11 |
| 28.6 | 22 |
| 29.2 | 12 |
| 29.4 | 13 |

Example 2: Preparation of Cabotegravir Sodium Form C

Cabotegravir sodium Form A (25 mg, prepared according to Reference Example 1 herein) was suspended in methylisobutyl ketone (2.5 mL) and heated to reflux temperature, whereat no complete dissolution occurred but the mixture remained a suspension. Said suspension was allowed to cool to room temperature and vigorously stirred at room temperature using a magnetic stirrer. After 7 days, the solid was collected by filtration dried under vacuum (30 mbar) at room temperature for 20 hours and analyzed by PXRD.

PXRD was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40 s per step (255 channels) in the angular range of 2° to 40° 2-theta at ambient conditions. A typical precision of the 2-theta values is in the range of ±0.2° 2-Theta, preferably of ±0.1° 2-Theta. Thus, the diffraction peak of cabotegravir sodium Form C that appears for example at 6.2° 2-Theta can appear in the range of from 6.0 to 6.4° 2-Theta, preferably in the range of from 6.1 to 6.3° 2-Theta on most X-ray diffractometers under standard conditions.

A representative diffractogram of cabotegravir sodium Form C is displayed in FIG. 5 herein. The corresponding reflection list is provided in Table 4 below.

TABLE 4

PXRD reflections and corresponding relative intensities of cabotegravir sodium Form C in the range of from 2 to 30° 2-Theta; A typical precision of the 2-Theta values is in the range of ±0.2° 2-Theta, preferably of ±0.1° 2-Theta.

| Reflection position [° 2-Theta] | Relative intensity [%] |
|---|---|
| 6.2 | 100 |
| 9.1 | 3 |
| 11.7 | 5 |
| 12.9 | 3 |
| 13.2 | 6 |
| 13.6 | 8 |
| 14.1 | 6 |
| 14.6 | 2 |
| 15.5 | 3 |
| 16.1 | 2 |
| 16.4 | 7 |
| 16.8 | 2 |
| 17.3 | 30 |
| 18.3 | 6 |
| 18.6 | 4 |
| 19.3 | 7 |
| 19.5 | 3 |
| 19.8 | 7 |
| 19.9 | 4 |
| 20.1 | 3 |
| 20.4 | 3 |
| 21.7 | 21 |
| 21.9 | 2 |
| 22.2 | 6 |
| 22.8 | 7 |
| 23.2 | 32 |
| 23.5 | 6 |
| 23.8 | 3 |
| 24.2 | 5 |
| 24.5 | 3 |
| 24.7 | 3 |
| 25.1 | 14 |
| 25.7 | 1 |
| 26.0 | 6 |
| 27.2 | 4 |
| 27.6 | 4 |
| 27.9 | 2 |
| 28.4 | 1 |
| 29.5 | 6 |

Example 3: Preparation of Cabotegravir Sodium Form C

Cabotegravir sodium Form A (204 mg, prepared according to Reference Example 1 herein) was suspended in methylisobutyl ketone (20 mL) and warmed to 60° C. The suspension was vigorously stirred at 60° C. using a magnetic stirrer. After 2 days, the solid was collected by filtration dried under vacuum (30 mbar) at room temperature for 20 hours and analyzed by PXRD, which confirmed the receipt of Form C.

Example 4: Thermogravimetric Analysis (TGA) of Forms A, B and C of Cabotegravir Sodium TGA was performed on a Mettler TGA/DSC 1 instrument. The samples (3.82 mg of Form A, 4.79 mg of Form B, 7.07 mg of Form C) were heated in a 100 microL aluminium pan closed with an aluminium lid, whereat the lid was automatically pierced at the beginning of the measurement. The samples were heated from 25 to 380° C. at a rate of 10 K/min. Nitrogen (purge rate 50 mL/min) was used as purge gas.

Figure 8:
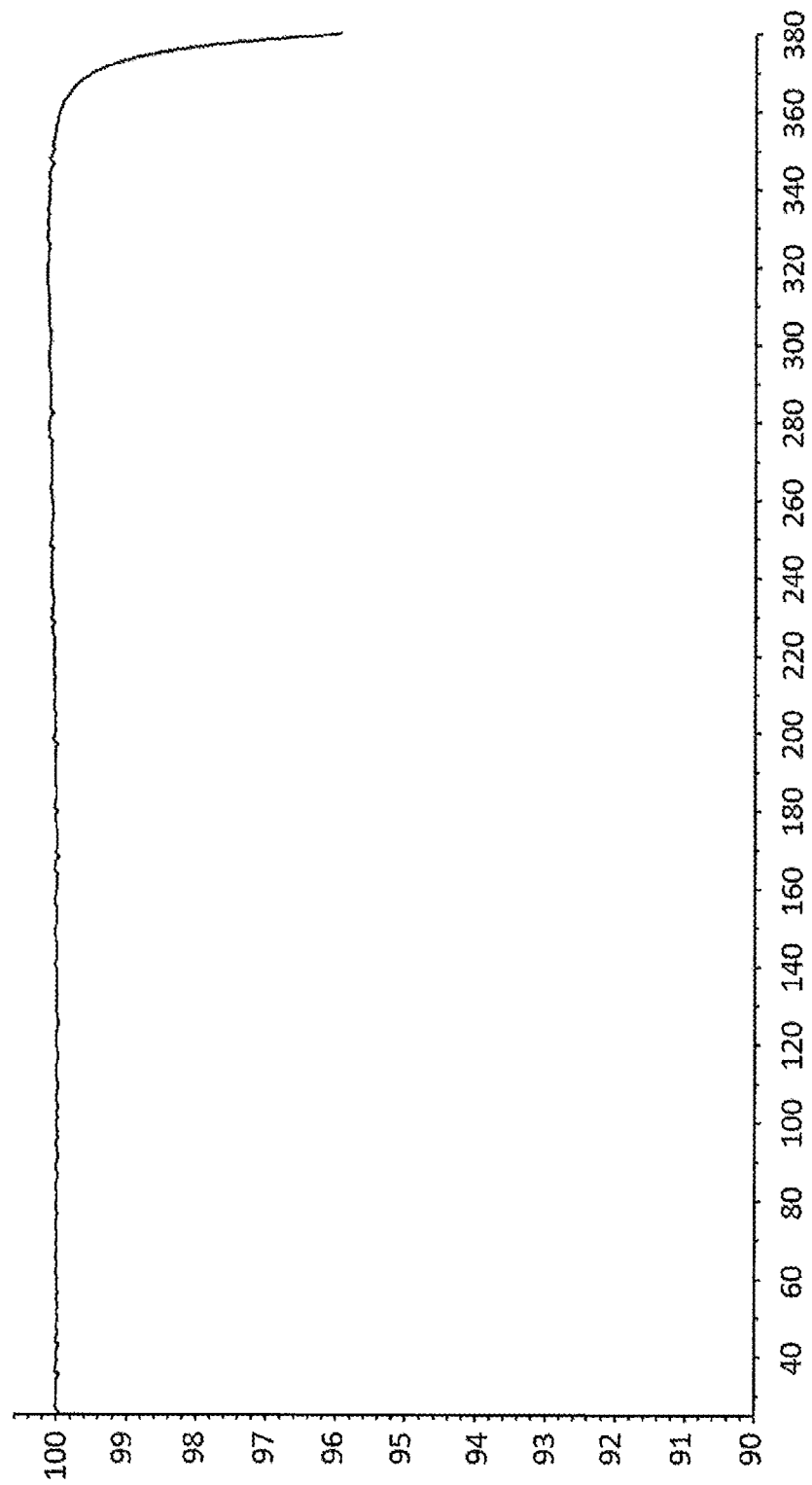
FIG. 8: illustrates a representative thermogravimetric analysis (TGA) curve of crystalline Form A of cabotegravir sodium prepared according to Reference Example 1 herein. The x-axis shows the temperature in degree Celsius (° C.), the y-axis shows the mass (loss) of the sample in weight percent (w-%).
Figure 9:
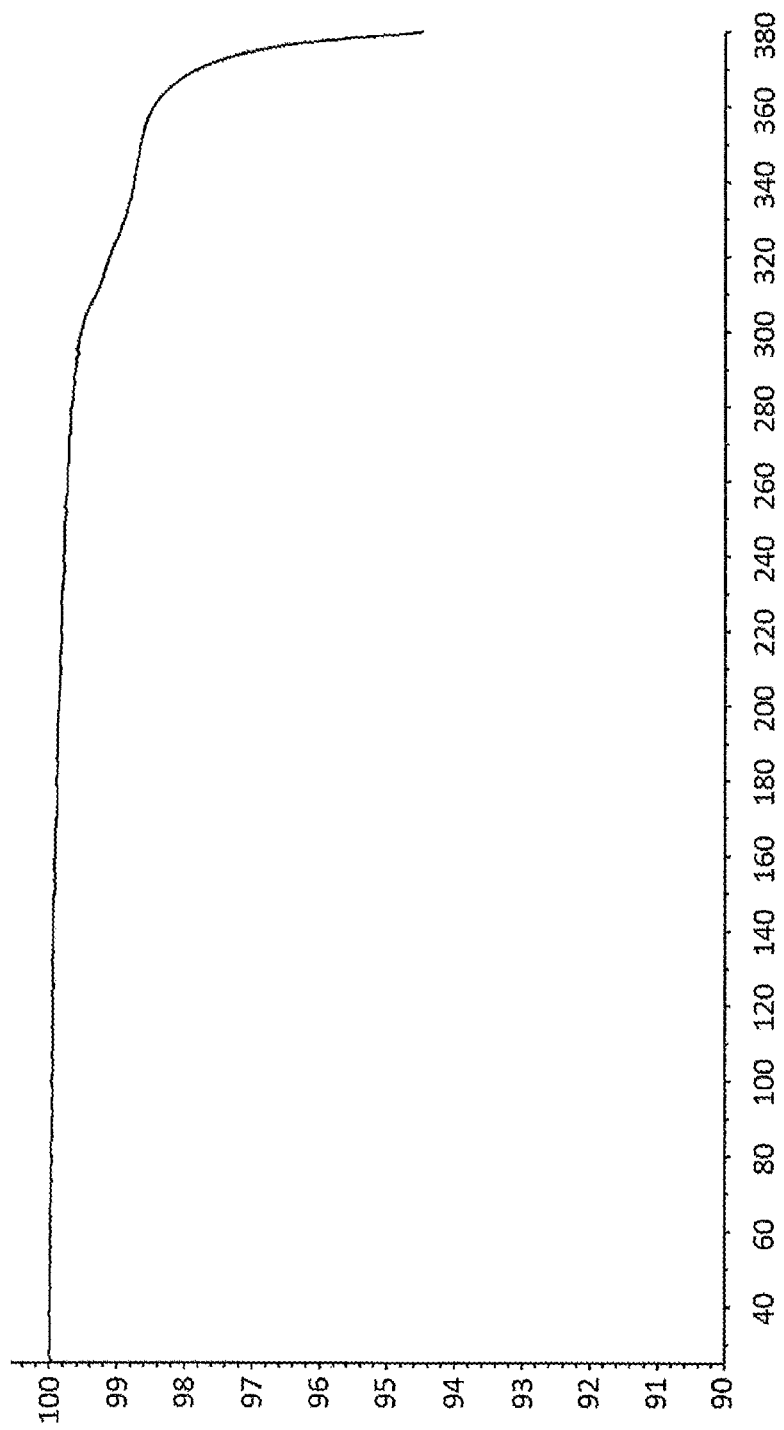
FIG. 9: illustrates a representative thermogravimetric analysis (TGA) curve of crystalline Form B of cabotegravir sodium of the present invention. The x-axis shows the temperature in degree Celsius (° C.), the y-axis shows the mass (loss) of the sample in weight percent (w-%).
Figure 10:
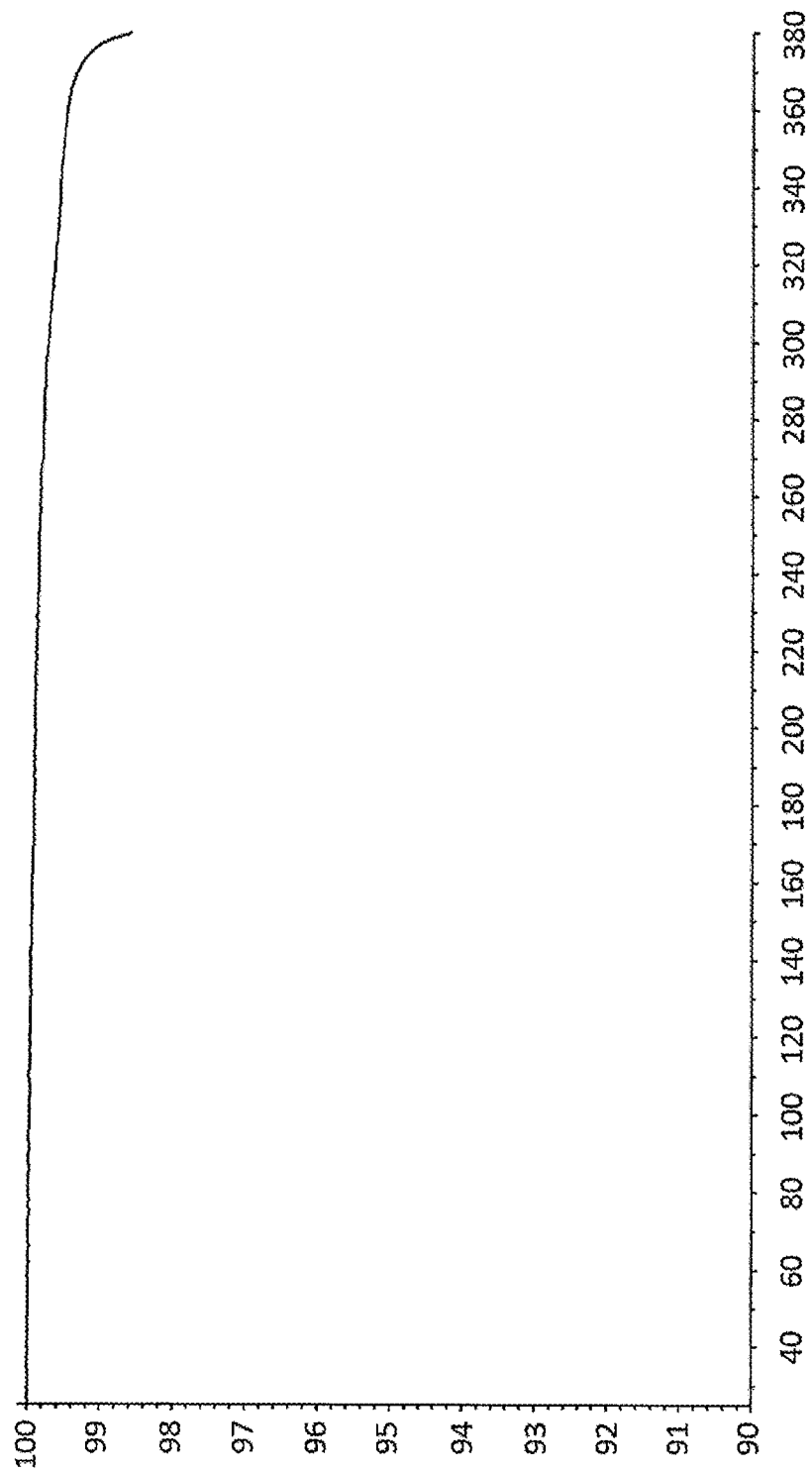
FIG. 10: illustrates a representative thermogravimetric analysis (TGA) curve of crystalline Form C of cabotegravir sodium of the present invention. The x-axis shows the temperature in degree Celsius (° C.), the y-axis shows the mass (loss) of the sample in weight percent (w-%).

The TGA curves of Forms A, B and C, which are displayed in FIGS. 8, 9 and 10 herein, show no significant mass loss (≤0.1 weight %) up to a temperature of about 200° C. confirming the presence of non-solvated and anhydrous forms.

Example 5: Competitive Slurry Experiment with Form A and Form B

Competitive slurry experiments in 2-butanone were performed by suspending equal amounts of Form A (approximately 50 mg, prepared according to Reference Example 1 herein) and Form B (approximately 50 mg, prepared according to Example 1 herein) in 2-butanone (4 mL) and vigorously stirring the obtained suspension using a magnetic stirrer at 20° C.; 40° C., 60° C. and 80° C. respectively. The results of the slurry experiments are summarized in Table 5 below.

TABLE 5

Overview of competitive slurry experiments performed with Form A and Form B

| Temperature | Sample 1 after 1 day | Sample 2 after 2 days | Sample 3 after 6 days |
|---|---|---|---|
| 20° C. | Form B | Form B | Form B |
| 40° C. | Form B | Form B | Form B |
| 60° C. | Form B | Form B | Form B |
| 80° C. | Form B | Form B | Form B |

The fact that in all experiments Form A completely converted to Form B suggests that Form B is thermodynamically more stable than Form A.

Reference Example 1: Experimental Repetition of the Final Step of Example Z-9

Cabotegravir (278 mg, 0.66 mmol e.g. prepared according to the procedure disclosed in Example Z-9, which is referring to Example Z-1 of WO 2006/116764 A1) was taken up in ethanol (10 mL) and treated with 1 N sodium hydroxide (aq) (0.66 mL, 0.66 mmol). The resulting suspension was stirred at room temperature for 30 minutes. Ether was added and the solid was collected by filtration. The obtained white solid was investigated by PXRD and found to be crystalline. Said crystalline material is designated Form A in the course of the present invention.

PXRD was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40 s per step (255 channels) in the angular range of 2° to 40° 2-theta at ambient conditions.

Figure 2:
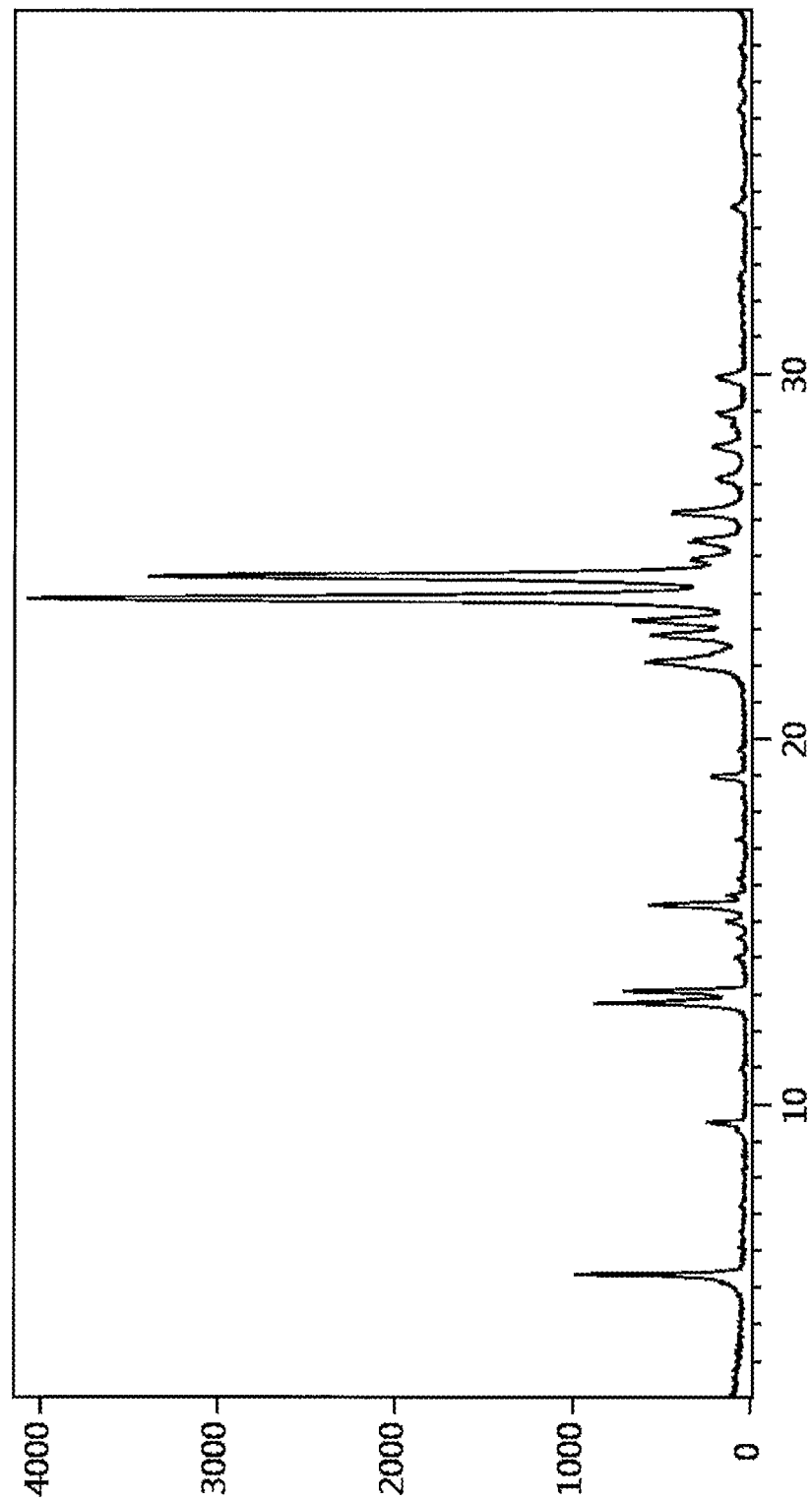
FIG. 2: illustrates a representative powder X-ray diffractogram of cabotegravir sodium Form A prepared according to Reference Example 1 herein. The x-axis shows the scattering angle in ° 2-Theta, the y-axis shows the intensity of the scattered X-ray beam in counts of detected photons.

A representative diffractogram of cabotegravir sodium Form A is displayed in FIG. 2 herein. The corresponding reflection list is provided in Table 6 below.

TABLE 6

PXRD reflections and corresponding relative intensities of cabotegravir sodium Form A in the range of from 2 to 30° 2-Theta; A typical precision of the 2-Theta values is in the range of ±0.2° 2-Theta, preferably of ±0.1° 2-Theta.

| Reflection position [° 2-Theta] | Relative intensity [%] |
| --- | --- |
| 5.4 | 25 |
| 9.5 | 6 |
| 12.8 | 21 |
| 13.1 | 18 |
| 15.5 | 13 |
| 19.0 | 5 |
| 22.1 | 13 |
| 22.8 | 13 |
| 23.3 | 16 |
| 23.9 | 100 |
| 24.4 | 81 |
| 24.9 | 8 |
| 25.5 | 7 |
| 26.2 | 10 |

Reference Example 2: Experimental Repetition of Example Ae of WO 2010/068253 A1

After dissolution of cabotegravir (254 mg, 0.60 mmol, e.g. prepared according to Example Aa to Ad of WO 2010/068253 A1) in ethanol (40 mL) and water (10 mL) by heating, followed by filtration, 1 N sodium hydroxide (aq) (0.61 mL, 0.61 mmol) was added to the solution at 75° C. The solution was gradually cooled to room temperature. Filtration, washing with ethanol (1.25 mL) and drying provided dolutegravir sodium crystals. The obtained crystals were analyzed by PXRD and could be assigned to Form A.

Reference Example 3: Experimental Repetition of J. Med. Chem. 2013, 56, 5901-5916

Cabotegravir (385 mg, 0.95 mmol) was treated with 1.0 N sodium hydroxide (aq) (0.95 mL, 0.95 mmol) in ethanol (15 mL) to obtain cabotegravir sodium (380 mg, yield 93% of theory) as a white solid. The obtained material was analyzed by PXRD and could be assigned to Form A.

Reference Example 4: Salt Formation in Methanol

Cabotegravir (1002 mg, 2.47 mmol) was treated with 2.0 N sodium hydroxide (aq) (1.25 mL, 2.50 mmol) in methanol (60 mL) at 60° C. and the reaction mixture was stirred further for 1 hour. The reaction mixture was cooled to room temperature and stirred for 1 hour. The solid was isolated by filtration, washed with methanol and dried. The obtained material was analyzed by PXRD and could be assigned to Form A.

The invention claimed is:

1. A composition comprising
a first crystalline form of cabotegravir sodium characterized by having a powder X-ray diffractogram comprising reflections at 2-Theta angles of:
(6.8±0.2)°, (18.5±0.2)° and (23.7±0.2)°; or
(6.8±0.2)°, (18.5±0.2)°, (20.3±0.2)° and (23.7±0.2)°; or
(6.8±0.2)°, (18.5±0.2)°, (18.9±0.2)°, (20.3±0.2)° and (23.7±0.2)°;
when measured at a temperature in the range of from 20 to 30° C. with Cu-Kalpha$_{1,2}$ radiation having a wavelength of 0.15419 nm, and
a second form of cabotegravir sodium in an amount up to 20 weight %, based on the weight of the composition, wherein the second form of cabotegravir sodium is amorphous cabotegravir sodium or crystalline Form A characterized by having a powder X-ray diffractogram comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm,
and wherein the composition comprises at most 20 weight % of the second form of cabotegravir sodium, based on the weight of the composition.

2. The composition of claim 1, wherein the first crystalline form of cabotegravir sodium is characterized by having a powder X-ray diffractogram essentially the same as shown in FIG. 1 of the present invention, when measured at a temperature in the range of from 20 to 30° C. with Cu-Kalpha$_{1,2}$ radiation having a wavelength of 0.15419 nm.

3. A process for the preparation of a crystalline form of cabotegravir sodium comprising:
(i) providing a crystalline form of cabotegravir sodium (Form A) characterized by having a PXRD comprising reflections at 2-Theta angles of (5.4±0.2)°, (12.8±0.2)°, (13.1±0.2)°, (23.9±0.2)° and (24.4±0.2)°, when measured at a temperature in the range of from 20 to 30° C. with Cu-Kalpha$_{1,2}$ radiation having a wavelength of 0.15419 nm.
(ii) slurrying the crystalline form of cabotegravir sodium (Form A) provided in step (i) in a solvent selected from the group consisting of cyclic ethers, $C_3$-$C_4$ ketones and methyl acetate or mixtures thereof, wherein the slurrying is for a time sufficient to effect transformation of cabotegravir sodium (Form A) to a crystalline form of cabotegravir sodium characterized by having a powder X-ray diffractogram comprising reflections at 2-Theta angles of:
(6.8±0.2)°, (18.5±0.2)° and (23.7±0.2)°; or
(6.8±0.2)°, (18.5±0.2)°, (20.3±0.2)° and (23.7±0.2)°; or
(6.8±0.2)°, (18.5±0.2)°, (18.9±0.2)°, (20.3±0.2)° and (23.7±0.2)°;
when measured at a temperature in the range of from 20 to 30° C. with Cu-Kalpha$_{1,2}$ radiation having a wavelength of 0.15419 nm.

4. The process of claim 3, wherein the cyclic ethers are selected from 1,4-dioxane and tetrahydrofuran and the $C_3$-$C_4$ ketones are selected from acetone and 2-butanone.

5. The process of claim 3, further comprising step (iii) separating at least a part of the crystals obtained in step (ii) from the mother liquor.

6. The process of claim 5, further comprising step (iv) washing the isolated crystals obtained in step (iii).

7. The process according to claim 3, further comprising step (v) drying the crystals obtained in step (ii).

8. The process according to claim 3, further comprising a step of mixing the crystalline form of cabotegravir sodium with at least one pharmaceutically acceptable excipient, to prepare a pharmaceutical composition.

9. The pharmaceutical process of claim 8, wherein the pharmaceutical composition is prepared as an oral solid dosage form, optionally a tablet or a capsule.

10. A method of therapeutic and/or prophylactic treatment, comprising a step of providing a composition according to claim 1 and a step of administering said composition to a person in need of such treatment, wherein the treatment is against viral infections.

11. The method according to claim 10 wherein said viral infections caused by any one selected from DNA viruses, RNA viruses, herpesviruses, retroviruses, hepadnaviruses, papillomavirus, hantavirus, adenoviruses and HIV.

* * * * *